US012775009B2

(12) United States Patent
Koussa et al.

(10) Patent No.: US 12,775,009 B2
(45) Date of Patent: Oct. 27, 2026

(54) MULTIPLEXED ANALYTE DETECTION

(71) Applicant: VITAL BIOSCIENCES INC., Mississauga (CA)

(72) Inventors: Mounir A. Koussa, Mississauga (CA); Aaron Witham, Mississauga (CA)

(73) Assignee: VITAL BIOSCIENCES INC., Mississauga (CA)

( * ) Notice: Subject to any disclaimer, the term of this patent is extended or adjusted under 35 U.S.C. 154(b) by 519 days.

(21) Appl. No.: 18/040,559

(22) PCT Filed: Aug. 6, 2021

(86) PCT No.: PCT/IB2021/057294

§ 371 (c)(1),
(2) Date: Feb. 3, 2023

(87) PCT Pub. No.: WO2022/029731

PCT Pub. Date: Feb. 10, 2022

(65) Prior Publication Data

US 2024/0295549 A1 Sep. 5, 2024

Related U.S. Application Data

(60) Provisional application No. 63/063,028, filed on Aug. 7, 2020.

(51) Int. Cl.
*G01N 33/543* (2006.01)
*G01N 33/68* (2006.01)

(52) U.S. Cl.
CPC ... *G01N 33/54333* (2013.01); *G01N 33/6854* (2013.01)

(58) Field of Classification Search
None
See application file for complete search history.

(56) References Cited

U.S. PATENT DOCUMENTS

| | | | |
|---|---|---|---|
| 4,141,687 | A | 2/1979 | Forrest et al. |
| 5,256,543 | A | 10/1993 | Pouletty et al. |
| 5,683,875 | A | 11/1997 | Lichtenwalter |
| 5,693,233 | A | 12/1997 | Schembri |
| 5,776,487 | A | 7/1998 | Maxfield Wilson et al. |
| 5,807,758 | A | 9/1998 | Lee et al. |
| 5,945,345 | A | 8/1999 | Blatt et al. |
| 5,948,624 | A | 9/1999 | Rothschild et al. |
| 6,103,537 | A | 8/2000 | Ullman et al. |
| 6,143,493 | A | 11/2000 | Stüber et al. |
| 6,265,229 | B1 | 7/2001 | Fodstad et al. |
| 6,291,249 | B1 | 9/2001 | Mahant et al. |
| 6,361,958 | B1 | 3/2002 | Shieh et al. |
| 6,417,011 | B1 | 7/2002 | Miltenyi |
| 6,444,261 | B1 | 9/2002 | Plaksine et al. |
| 6,468,657 | B1 | 10/2002 | Hou et al. |
| 6,479,302 | B1 | 11/2002 | Dremel |
| 6,551,841 | B1 | 4/2003 | Wilding et al. |
| 6,569,647 | B1 | 5/2003 | Zhang et al. |
| 6,607,922 | B2 | 8/2003 | LaBorde |
| 6,649,419 | B1 | 11/2003 | Anderson |
| 6,746,661 | B2 | 6/2004 | Kaplan |
| 6,930,292 | B1 | 8/2005 | Winther et al. |
| 6,960,467 | B2 | 11/2005 | Shieh et al. |
| 7,005,292 | B2 | 2/2006 | Wilding et al. |
| 7,018,830 | B2 | 3/2006 | Wilding et al. |
| 7,074,586 | B1 | 7/2006 | Cheronis et al. |
| 7,113,069 | B1 | 9/2006 | Sunshine et al. |
| 7,179,660 | B1 | 2/2007 | Kirakossian et al. |
| 7,271,265 | B2 | 9/2007 | Haugland et al. |
| 7,413,909 | B2 | 8/2008 | Hutchens et al. |
| 7,416,889 | B2 | 8/2008 | Ciomber et al. |
| 7,510,865 | B2 | 3/2009 | Yoo et al. |
| 7,527,980 | B2 | 5/2009 | Haik |
| 7,572,640 | B2 | 8/2009 | Goix et al. |
| 7,635,585 | B2 | 12/2009 | Yoo |
| 7,692,794 | B2 | 4/2010 | Kim et al. |
| 7,718,421 | B2 | 5/2010 | Chen et al. |
| 7,732,153 | B2 | 6/2010 | Akhavan-Tafti |
| 7,749,442 | B2 | 7/2010 | Koike et al. |
| 7,799,534 | B2 | 9/2010 | Akhavan-Tafti |
| 7,838,250 | B1 | 11/2010 | Goix et al. |
| 7,842,515 | B2 | 11/2010 | Zou et al. |
| 7,855,054 | B2 | 12/2010 | Schneider et al. |
| 7,863,022 | B2 | 1/2011 | Prins et al. |
| 7,914,734 | B2 | 3/2011 | Livingston |
| 7,923,213 | B2 | 4/2011 | Akhavan-Tafti |
| 7,923,214 | B2 | 4/2011 | Akhavan-Tafti |
| 8,076,092 | B2 | 12/2011 | Akhavan-Tafti |

(Continued)

FOREIGN PATENT DOCUMENTS

| | | |
|---|---|---|
| CA | 2820181 A1 | 1/2014 |
| CA | 3110308 A1 | 2/2020 |

(Continued)

OTHER PUBLICATIONS

Molecular Probes™ Handbook Chapter 4 Biotin and Hapten Derivatives. ThermoFisher Scientific, 2010, (21 pages), https://www.thermofisher.com/content/dam/LifeTech/global/technical-reference-library/Molecular%20Probes%20Handbook/chapter-pdfs/Ch-4-Biotin-Hapten-Derivatives.pdf?ici.*

(Continued)

*Primary Examiner* — Ellen J Marcsisin
(74) *Attorney, Agent, or Firm* — Morgan, Lewis & Bockius LLP

(57) ABSTRACT

Methods and kits for multiplexed detection of presence, absence, or amount of a plurality of analytes in a biological sample are provided.

20 Claims, 7 Drawing Sheets

Specification includes a Sequence Listing.

(56) References Cited

U.S. PATENT DOCUMENTS

| | | | |
|---|---|---|---|
| 8,088,586 | B2 | 1/2012 | Barnardo et al. |
| 8,101,138 | B2 | 1/2012 | Lee et al. |
| 8,114,662 | B2 | 2/2012 | Clark et al. |
| 8,124,362 | B2 | 2/2012 | Tafti |
| 8,188,243 | B2 | 5/2012 | Bard et al. |
| 8,190,372 | B2 | 5/2012 | Kahlman et al. |
| 8,263,386 | B2 | 9/2012 | Yoo |
| 8,264,684 | B2 | 9/2012 | Livingston |
| 8,278,057 | B2 | 10/2012 | Singh et al. |
| 8,283,912 | B2 | 10/2012 | Nieuwenhuis et al. |
| 8,287,809 | B2 | 10/2012 | Gould et al. |
| 8,287,810 | B2 | 10/2012 | Alocilja et al. |
| 8,343,728 | B2 | 1/2013 | Goix et al. |
| 8,357,671 | B2 | 1/2013 | Paulson et al. |
| 8,409,877 | B2 | 4/2013 | Liu et al. |
| 8,449,833 | B2 | 5/2013 | Nieuwenhuis |
| 8,450,069 | B2 | 5/2013 | Goix et al. |
| 8,462,339 | B2 | 6/2013 | Livingston |
| 8,512,966 | B2 | 8/2013 | Carter et al. |
| 8,520,211 | B2 | 8/2013 | Schleipen et al. |
| 8,524,504 | B2 | 9/2013 | Carter et al. |
| 8,535,895 | B2 | 9/2013 | Goix et al. |
| 8,617,798 | B2 | 12/2013 | Mason et al. |
| 8,618,508 | B2 | 12/2013 | Wimberger-Friedl et al. |
| 8,628,729 | B2 | 1/2014 | Carrilho et al. |
| 8,634,075 | B2 | 1/2014 | Livingston |
| 8,664,008 | B2 | 3/2014 | Liu et al. |
| 8,669,110 | B2 | 3/2014 | Dehal et al. |
| 8,685,711 | B2 | 4/2014 | Goix et al. |
| 8,741,230 | B2 | 6/2014 | Holmes et al. |
| 8,758,686 | B2 | 6/2014 | Carter et al. |
| 8,797,028 | B2 | 8/2014 | Verschuren et al. |
| 8,828,740 | B2 | 9/2014 | Kahlman et al. |
| 8,841,070 | B2 | 9/2014 | Harnack et al. |
| 8,871,917 | B2 | 10/2014 | Bard et al. |
| 8,873,038 | B2 | 10/2014 | Kodali et al. |
| 8,911,684 | B2 | 12/2014 | Augstein et al. |
| 8,917,392 | B2 | 12/2014 | Livingston |
| 8,921,118 | B2 | 12/2014 | Siegel et al. |
| 8,932,811 | B2 | 1/2015 | Van De Stolpe et al. |
| 8,936,946 | B2 | 1/2015 | Alocilja et al. |
| 8,951,749 | B2 | 2/2015 | Rylatt et al. |
| 8,986,926 | B2 | 3/2015 | Ferree et al. |
| 8,993,487 | B2 | 3/2015 | Yoo |
| 9,023,651 | B2 | 5/2015 | Evers et al. |
| 9,040,305 | B2 | 5/2015 | Goix et al. |
| 9,046,514 | B2 | 6/2015 | Sista et al. |
| 9,056,318 | B2 | 6/2015 | Bergman et al. |
| 9,057,723 | B2 | 6/2015 | Carter et al. |
| 9,063,131 | B2 | 6/2015 | Goix et al. |
| 9,068,991 | B2 | 6/2015 | Goix et al. |
| 9,075,041 | B2 | 7/2015 | Kavusi et al. |
| 9,101,301 | B2 | 8/2015 | Papadimitrakopoulos et al. |
| 9,103,843 | B2 | 8/2015 | Nieuwenhuis et al. |
| 9,128,084 | B2 | 9/2015 | Prins et al. |
| 9,134,201 | B2 | 9/2015 | Van Lankvelt et al. |
| 9,157,891 | B2 | 10/2015 | Ovsyanko et al. |
| 9,164,091 | B2 | 10/2015 | Kim |
| 9,180,453 | B2 | 11/2015 | Chiu et al. |
| 9,182,405 | B2 | 11/2015 | Goix et al. |
| 9,207,210 | B2 | 12/2015 | Ovsyanko |
| 9,239,284 | B2 | 1/2016 | Livingston |
| 9,254,488 | B2 | 2/2016 | Nieuwenhuis et al. |
| 9,267,167 | B2 | 2/2016 | Lizzi et al. |
| 9,274,105 | B2 | 3/2016 | Guo et al. |
| 9,304,130 | B2 | 4/2016 | Boday et al. |
| 9,328,343 | B2 | 5/2016 | Dressman et al. |
| 9,329,175 | B2 | 5/2016 | Miller et al. |
| 9,333,276 | B2 | 5/2016 | Guelcher et al. |
| 9,371,563 | B2 | 6/2016 | Geiss et al. |
| 9,371,596 | B2 | 6/2016 | Faure et al. |
| 9,387,484 | B2 | 7/2016 | Wimberger-Friedl et al. |
| 9,404,919 | B2 | 8/2016 | Schneider et al. |
| 9,410,948 | B2 | 8/2016 | Dittmer |
| 9,442,117 | B2 | 9/2016 | Bard et al. |
| 9,448,236 | B2 | 9/2016 | Alocilja et al. |
| 9,488,647 | B2 | 11/2016 | Van Zon et al. |
| 9,494,598 | B2 | 11/2016 | Goix et al. |
| 9,557,328 | B2 | 1/2017 | Dittmer et al. |
| 9,575,081 | B2 | 2/2017 | Nieuwenhuis et al. |
| 9,588,112 | B2 | 3/2017 | Evers |
| 9,603,544 | B2 | 3/2017 | Gleich |
| 9,612,236 | B2 | 4/2017 | Sabatte et al. |
| 9,658,219 | B2 | 5/2017 | Verschuren et al. |
| 9,908,116 | B2 | 3/2018 | Da Fonseca et al. |
| 10,018,584 | B2 | 7/2018 | Bohets |
| 10,031,053 | B2 | 7/2018 | Boehm |
| 10,232,105 | B2 | 3/2019 | Tenreiro et al. |
| 10,233,480 | B2 | 3/2019 | Loo et al. |
| 10,309,976 | B2 | 6/2019 | Johno et al. |
| 10,451,622 | B2 | 10/2019 | Melanson et al. |
| 10,525,470 | B2 | 1/2020 | Reis et al. |
| 10,639,635 | B2 | 5/2020 | Reis et al. |
| 10,661,276 | B2 | 5/2020 | Moura Pires De Andrade Tenreiro et al. |
| 10,845,305 | B1 | 11/2020 | Ruckh et al. |
| 11,285,479 | B2 | 3/2022 | Moura Pires De Andrade Tenreiro et al. |
| 11,366,083 | B2 | 6/2022 | Wei |
| 11,964,274 | B2 | 4/2024 | Reis et al. |
| 12,013,366 | B2 | 6/2024 | Clausen et al. |
| 2001/0049111 | A1 | 12/2001 | Windhab et al. |
| 2002/0009738 | A1 | 1/2002 | Houghton et al. |
| 2002/0028519 | A1 | 3/2002 | Yguerabide et al. |
| 2002/0045276 | A1 | 4/2002 | Yguerabide et al. |
| 2002/0058019 | A1 | 5/2002 | Berenson et al. |
| 2002/0076154 | A1 | 6/2002 | Maisenhoelder et al. |
| 2002/0094548 | A1 | 7/2002 | Feistel |
| 2002/0106314 | A1 | 8/2002 | Pelrine et al. |
| 2002/0119447 | A1 | 8/2002 | Simons et al. |
| 2002/0123134 | A1 | 9/2002 | Huang et al. |
| 2002/0136668 | A1 | 9/2002 | Wallace et al. |
| 2002/0160363 | A1 | 10/2002 | McDevitt et al. |
| 2002/0168663 | A1 | 11/2002 | Phan et al. |
| 2002/0172987 | A1 | 11/2002 | Terstappen et al. |
| 2002/0177144 | A1 | 11/2002 | Remacle et al. |
| 2002/0197645 | A1 | 12/2002 | Martin |
| 2003/0040129 | A1 | 2/2003 | Shah |
| 2003/0066956 | A1 | 4/2003 | Gruber et al. |
| 2003/0092090 | A1 | 5/2003 | Hajizadeh et al. |
| 2003/0094369 | A1 | 5/2003 | Tolley et al. |
| 2003/0124592 | A1 | 7/2003 | Puskas |
| 2003/0129749 | A1 | 7/2003 | Gundersen et al. |
| 2003/0134416 | A1 | 7/2003 | Yamanishi et al. |
| 2003/0142901 | A1 | 7/2003 | Lahann et al. |
| 2003/0157731 | A1 | 8/2003 | Yguerabide et al. |
| 2003/0170631 | A1 | 9/2003 | Houghton et al. |
| 2003/0186323 | A1 | 10/2003 | Vogel et al. |
| 2003/0207328 | A1 | 11/2003 | Yguerabide et al. |
| 2004/0005723 | A1 | 1/2004 | Empedocles et al. |
| 2004/0009614 | A1 | 1/2004 | Ahn et al. |
| 2004/0018519 | A1 | 1/2004 | Wright, Jr. |
| 2004/0043509 | A1 | 3/2004 | Stalher et al. |
| 2004/0058389 | A1 | 3/2004 | Wang et al. |
| 2004/0142463 | A1 | 7/2004 | Walker et al. |
| 2004/0147031 | A1 | 7/2004 | Nakao |
| 2004/0166514 | A1 | 8/2004 | Puskas |
| 2004/0166553 | A1 | 8/2004 | Nguyen et al. |
| 2004/0181343 | A1 | 9/2004 | Wigstrom et al. |
| 2004/0219580 | A1 | 11/2004 | Dunn et al. |
| 2004/0253632 | A1 | 12/2004 | Rhode et al. |
| 2005/0003346 | A1 | 1/2005 | Voorhees et al. |
| 2005/0003559 | A1 | 1/2005 | Weber et al. |
| 2005/0064395 | A1 | 3/2005 | Israel et al. |
| 2005/0074774 | A1 | 4/2005 | Woudenberg et al. |
| 2005/0079598 | A1 | 4/2005 | Davis |
| 2005/0129727 | A1 | 6/2005 | Weber et al. |
| 2005/0158723 | A1 | 7/2005 | Viovy et al. |
| 2005/0164205 | A1 | 7/2005 | Puskas |
| 2005/0222504 | A1 | 10/2005 | Otvos et al. |
| 2005/0232929 | A1 | 10/2005 | Kadkhodayan et al. |
| 2005/0239108 | A1 | 10/2005 | Barletta et al. |

(56) References Cited

U.S. PATENT DOCUMENTS

| | | | |
|---|---|---|---|
| 2005/0244850 | A1 | 11/2005 | Huang et al. |
| 2005/0250220 | A1 | 11/2005 | Kozulic |
| 2005/0255464 | A1 | 11/2005 | Hagen et al. |
| 2005/0261479 | A1 | 11/2005 | Hoffmann et al. |
| 2005/0266417 | A1 | 12/2005 | Barany et al. |
| 2005/0272110 | A1 | 12/2005 | Drukier |
| 2006/0003333 | A1 | 1/2006 | Puskas |
| 2006/0008206 | A1 | 1/2006 | Maisenholder et al. |
| 2006/0024722 | A1 | 2/2006 | Fischer-Colbrie et al. |
| 2006/0025713 | A1 | 2/2006 | Rosengart et al. |
| 2006/0078998 | A1 | 4/2006 | Puskas et al. |
| 2006/0131542 | A1 | 6/2006 | Weng et al. |
| 2006/0177882 | A1 | 8/2006 | Talebpour et al. |
| 2006/0194327 | A1 | 8/2006 | Kahlan et al. |
| 2006/0199273 | A1 | 9/2006 | Rabe et al. |
| 2006/0210987 | A1 | 9/2006 | Gleich |
| 2006/0216238 | A1 | 9/2006 | Manchester et al. |
| 2006/0240572 | A1* | 10/2006 | Carron ................. G01N 21/658 436/524 |
| 2006/0263832 | A1 | 11/2006 | Shang et al. |
| 2006/0281102 | A1 | 12/2006 | Puskas |
| 2007/0003528 | A1 | 1/2007 | Consigny et al. |
| 2007/0020620 | A1 | 1/2007 | Finn et al. |
| 2007/0020649 | A1 | 1/2007 | Tseng et al. |
| 2007/0116682 | A1 | 5/2007 | Atala et al. |
| 2007/0116683 | A1 | 5/2007 | Atala et al. |
| 2007/0116684 | A1 | 5/2007 | Atala et al. |
| 2007/0161121 | A1 | 7/2007 | Schuchard et al. |
| 2007/0161124 | A1 | 7/2007 | Schuchard et al. |
| 2007/0166740 | A1 | 7/2007 | Heil et al. |
| 2007/0166741 | A1 | 7/2007 | Heil et al. |
| 2007/0191819 | A1 | 8/2007 | Steinfeld et al. |
| 2007/0191963 | A1 | 8/2007 | Winterbottom et al. |
| 2007/0231790 | A1 | 10/2007 | Su |
| 2007/0275396 | A1 | 11/2007 | Zheng |
| 2008/0011977 | A1 | 1/2008 | Atwood |
| 2008/0021674 | A1 | 1/2008 | Puskas |
| 2008/0032420 | A1* | 2/2008 | Lambert .......... G01N 33/54388 436/514 |
| 2008/0039630 | A1 | 2/2008 | Haugland et al. |
| 2008/0139399 | A1 | 6/2008 | Fonnum et al. |
| 2008/0158543 | A1 | 7/2008 | Puskas et al. |
| 2008/0171352 | A1 | 7/2008 | Goix et al. |
| 2008/0187472 | A1 | 8/2008 | Ahn et al. |
| 2008/0196483 | A1 | 8/2008 | Kurt et al. |
| 2008/0199851 | A1 | 8/2008 | Egan et al. |
| 2008/0218165 | A1 | 9/2008 | Kahlman et al. |
| 2008/0268481 | A1 | 10/2008 | Prins et al. |
| 2008/0269069 | A1 | 10/2008 | Bacher et al. |
| 2008/0272516 | A1 | 11/2008 | Liu et al. |
| 2008/0280285 | A1 | 11/2008 | Chen et al. |
| 2008/0305489 | A1 | 12/2008 | Thomas et al. |
| 2008/0309329 | A1 | 12/2008 | Kahlman et al. |
| 2008/0314749 | A1 | 12/2008 | Johnson et al. |
| 2009/0028910 | A1 | 1/2009 | DeSimone et al. |
| 2009/0029478 | A1 | 1/2009 | Puskas |
| 2009/0054262 | A1 | 2/2009 | Abbott et al. |
| 2009/0081711 | A1 | 3/2009 | Singh |
| 2009/0087860 | A1 | 4/2009 | Todd et al. |
| 2009/0087862 | A1 | 4/2009 | Carter et al. |
| 2009/0088982 | A1 | 4/2009 | Fukushima et al. |
| 2009/0102472 | A1 | 4/2009 | Nieuwenhhuis et al. |
| 2009/0105087 | A1 | 4/2009 | Kahlman et al. |
| 2009/0117168 | A1 | 5/2009 | Keenan |
| 2009/0117670 | A1 | 5/2009 | Van Der Wijk et al. |
| 2009/0142772 | A1 | 6/2009 | Lau et al. |
| 2009/0148869 | A1 | 6/2009 | Zaugg et al. |
| 2009/0156422 | A1 | 6/2009 | Punyadeera et al. |
| 2009/0156423 | A1 | 6/2009 | Stahler et al. |
| 2009/0156428 | A1 | 6/2009 | Malcolm |
| 2009/0170212 | A1 | 7/2009 | Van Der Wijk et al. |
| 2009/0171590 | A1 | 7/2009 | Puskas et al. |
| 2009/0181402 | A1 | 7/2009 | Finn et al. |
| 2009/0186420 | A1 | 7/2009 | Kahlman et al. |
| 2009/0214618 | A1 | 8/2009 | Schoenfisch et al. |
| 2009/0216170 | A1 | 8/2009 | Robinson et al. |
| 2009/0219012 | A1 | 9/2009 | Nieuwenhuis et al. |
| 2009/0234202 | A1 | 9/2009 | Goix et al. |
| 2009/0253215 | A1 | 10/2009 | Hikmet et al. |
| 2009/0269858 | A1 | 10/2009 | Punyadeera et al. |
| 2009/0275031 | A1 | 11/2009 | Tanner et al. |
| 2009/0280571 | A1 | 11/2009 | Nieuwenhuis et al. |
| 2009/0301885 | A1 | 12/2009 | Guzman |
| 2009/0305290 | A1 | 12/2009 | Sambursky et al. |
| 2009/0325164 | A1 | 12/2009 | Vossenaar et al. |
| 2010/0022857 | A1 | 1/2010 | Ergeneman et al. |
| 2010/0087327 | A1 | 4/2010 | Weng et al. |
| 2010/0112727 | A1 | 5/2010 | Todd et al. |
| 2010/0152651 | A1 | 6/2010 | Boyden et al. |
| 2010/0159445 | A1 | 6/2010 | Lustig et al. |
| 2010/0194386 | A1 | 8/2010 | Prins et al. |
| 2010/0221842 | A1 | 9/2010 | Klumder et al. |
| 2010/0248973 | A1 | 9/2010 | Van Lankvelt et al. |
| 2010/0255518 | A1 | 10/2010 | Goix et al. |
| 2010/0261195 | A1 | 10/2010 | Rubenstein et al. |
| 2010/0267165 | A1 | 10/2010 | Bruls et al. |
| 2010/0272608 | A1 | 10/2010 | Penterman et al. |
| 2010/0273142 | A1 | 10/2010 | Prins et al. |
| 2010/0273269 | A1 | 10/2010 | Van Lankvelt et al. |
| 2010/0285606 | A1 | 11/2010 | Phillips et al. |
| 2010/0297780 | A1 | 11/2010 | De Theije et al. |
| 2010/0311085 | A1 | 12/2010 | Zaugg et al. |
| 2010/0322824 | A1 | 12/2010 | Neijzen |
| 2010/0323355 | A1 | 12/2010 | Dittmer |
| 2011/0020836 | A1 | 1/2011 | Li |
| 2011/0033522 | A1 | 2/2011 | Reinherz et al. |
| 2011/0045470 | A1 | 2/2011 | Murakami et al. |
| 2011/0065209 | A1 | 3/2011 | Heil et al. |
| 2011/0091903 | A1 | 4/2011 | Bommarito et al. |
| 2011/0107855 | A1 | 5/2011 | Motadel |
| 2011/0111428 | A1 | 5/2011 | Carter et al. |
| 2011/0117202 | A1 | 5/2011 | Bourke, Jr. et al. |
| 2011/0117668 | A1 | 5/2011 | Stayton et al. |
| 2011/0136099 | A1 | 6/2011 | Schneider et al. |
| 2011/0206560 | A1 | 8/2011 | Neijzen et al. |
| 2011/0207150 | A1 | 8/2011 | Zaugg et al. |
| 2011/0207171 | A1 | 8/2011 | Agnew et al. |
| 2011/0208040 | A1 | 8/2011 | Carmi et al. |
| 2011/0235037 | A1 | 9/2011 | Schleipen |
| 2011/0237704 | A1 | 9/2011 | Guelcher et al. |
| 2011/0256640 | A1 | 10/2011 | Dittmer et al. |
| 2011/0301053 | A1 | 12/2011 | Todd et al. |
| 2012/0019240 | A1 | 1/2012 | Müller et al. |
| 2012/0031773 | A1 | 2/2012 | Miller |
| 2012/0034633 | A1 | 2/2012 | Miller et al. |
| 2012/0034684 | A1 | 2/2012 | Emerson et al. |
| 2012/0062219 | A1 | 3/2012 | Craus |
| 2012/0082728 | A1 | 4/2012 | Schneider et al. |
| 2012/0100546 | A1 | 4/2012 | Lowery, Jr. et al. |
| 2012/0119727 | A1 | 5/2012 | Prins et al. |
| 2012/0135530 | A1 | 5/2012 | Bamdad et al. |
| 2012/0149128 | A1 | 6/2012 | Manneh |
| 2012/0156693 | A1 | 6/2012 | Wong et al. |
| 2012/0171781 | A1 | 7/2012 | Dittmer et al. |
| 2012/0178186 | A1 | 7/2012 | Nieuwenhuis et al. |
| 2012/0181176 | A1 | 7/2012 | Atwood |
| 2012/0184046 | A1 | 7/2012 | Atkin |
| 2012/0208296 | A1 | 8/2012 | Ranzoni et al. |
| 2012/0212733 | A1 | 8/2012 | Kodali et al. |
| 2012/0220051 | A1 | 8/2012 | Yin et al. |
| 2012/0258126 | A1 | 10/2012 | Schøller et al. |
| 2012/0262565 | A1 | 10/2012 | Kahlman et al. |
| 2012/0264133 | A1 | 10/2012 | Sambursky et al. |
| 2012/0282636 | A1 | 11/2012 | Altschul et al. |
| 2013/0034527 | A1 | 2/2013 | Hyde et al. |
| 2013/0088221 | A1 | 4/2013 | Van Zon et al. |
| 2013/0109030 | A1 | 5/2013 | Hardeman et al. |
| 2013/0109106 | A1 | 5/2013 | Klunder et al. |
| 2013/0122492 | A1 | 5/2013 | Khosravi et al. |
| 2013/0137117 | A1 | 5/2013 | Levi et al. |
| 2013/0196341 | A1 | 8/2013 | Neely et al. |
| 2013/0214040 | A1 | 8/2013 | Beerling et al. |
| 2013/0260367 | A1 | 10/2013 | Lowery, Jr. et al. |
| 2013/0260390 | A1 | 10/2013 | Goix et al. |

(56) References Cited

U.S. PATENT DOCUMENTS

| | | | |
|---|---|---|---|
| 2013/0266930 | A1 | 10/2013 | Dinges |
| 2013/0267039 | A1 | 10/2013 | Todd et al. |
| 2013/0267431 | A1 | 10/2013 | Singh et al. |
| 2013/0315783 | A1 | 11/2013 | Carter et al. |
| 2013/0316468 | A1 | 11/2013 | Todd et al. |
| 2014/0057366 | A1 | 2/2014 | Dittmer et al. |
| 2014/0065616 | A1 | 3/2014 | Xu |
| 2014/0094383 | A1 | 4/2014 | Lee et al. |
| 2014/0100102 | A1 | 4/2014 | Rajagopal et al. |
| 2014/0109972 | A1 | 4/2014 | Garcia Da Fonseca et al. |
| 2014/0120632 | A1 | 5/2014 | Ranzoni et al. |
| 2014/0127713 | A1 | 5/2014 | De Theije et al. |
| 2014/0127722 | A1 | 5/2014 | Ranzoni et al. |
| 2014/0147932 | A1 | 5/2014 | Goix et al. |
| 2014/0154257 | A1 | 6/2014 | DeChristopher |
| 2014/0170652 | A1 | 6/2014 | Sitdikov et al. |
| 2014/0170767 | A1 | 6/2014 | Lee et al. |
| 2014/0179025 | A1 | 6/2014 | Weng et al. |
| 2014/0186940 | A1 | 7/2014 | Goel |
| 2014/0193488 | A1 | 7/2014 | Kim et al. |
| 2014/0205996 | A1 | 7/2014 | Lizzi et al. |
| 2014/0206632 | A1 | 7/2014 | Todd et al. |
| 2014/0227715 | A1 | 8/2014 | Todd et al. |
| 2014/0251832 | A1 | 9/2014 | Porter |
| 2014/0274762 | A1 | 9/2014 | Manuguerra et al. |
| 2014/0295420 | A1 | 10/2014 | Ovsyanko et al. |
| 2014/0295432 | A1 | 10/2014 | Evers et al. |
| 2014/0302535 | A1 | 10/2014 | Lovell et al. |
| 2014/0308680 | A1 | 10/2014 | Van Lieshout |
| 2014/0328999 | A1 | 11/2014 | Aizenberg et al. |
| 2014/0330257 | A1 | 11/2014 | Hyde et al. |
| 2014/0335527 | A1 | 11/2014 | Goel |
| 2014/0342468 | A1 | 11/2014 | Todd et al. |
| 2014/0356129 | A1 | 12/2014 | Paust et al. |
| 2014/0363833 | A1 | 12/2014 | Bhatia et al. |
| 2014/0377771 | A1 | 12/2014 | Bibette et al. |
| 2014/0377789 | A1 | 12/2014 | Moerman |
| 2014/0377837 | A1 | 12/2014 | Agnew et al. |
| 2015/0024974 | A1 | 1/2015 | Banerjee et al. |
| 2015/0072396 | A1 | 3/2015 | Gee et al. |
| 2015/0093750 | A1 | 4/2015 | Ovsyanko et al. |
| 2015/0105284 | A1 | 4/2015 | Willson et al. |
| 2015/0119275 | A1 | 4/2015 | Todd et al. |
| 2015/0140684 | A1 | 5/2015 | Kim et al. |
| 2015/0141259 | A1 | 5/2015 | Sanders et al. |
| 2015/0160217 | A1 | 6/2015 | Wong et al. |
| 2015/0165092 | A1 | 6/2015 | Kaplan et al. |
| 2015/0168390 | A1 | 6/2015 | Maas et al. |
| 2015/0177239 | A1 | 6/2015 | Evers et al. |
| 2015/0187479 | A1 | 7/2015 | Van Lieshout et al. |
| 2015/0198532 | A1 | 7/2015 | Lee et al. |
| 2015/0226732 | A1 | 8/2015 | De Theije et al. |
| 2015/0233908 | A1 | 8/2015 | Kelly et al. |
| 2015/0299764 | A1 | 10/2015 | Raspe et al. |
| 2015/0316545 | A1 | 11/2015 | Peck et al. |
| 2015/0316549 | A2 | 11/2015 | Feldman et al. |
| 2015/0323523 | A1 | 11/2015 | Evers et al. |
| 2015/0329617 | A1 | 11/2015 | Winther et al. |
| 2016/0003814 | A1 | 1/2016 | Hamasaki et al. |
| 2016/0008788 | A1 | 1/2016 | Nassar |
| 2016/0010136 | A1 | 1/2016 | Nassar |
| 2016/0041166 | A1 | 2/2016 | Jablonski et al. |
| 2016/0054311 | A1 | 2/2016 | Marks et al. |
| 2016/0061826 | A1 | 3/2016 | Sohn et al. |
| 2016/0084762 | A1 | 3/2016 | Goix et al. |
| 2016/0091497 | A1 | 3/2016 | Goix et al. |
| 2016/0123965 | A1 | 5/2016 | Evers et al. |
| 2016/0178520 | A1 | 6/2016 | Livingston |
| 2016/0186253 | A1 | 6/2016 | Talasaz et al. |
| 2016/0195524 | A1 | 7/2016 | Cowan et al. |
| 2016/0202248 | A1 | 7/2016 | Lee et al. |
| 2016/0202270 | A1 | 7/2016 | Goix et al. |
| 2016/0216256 | A1 | 7/2016 | Miller et al. |
| 2016/0223530 | A1 | 8/2016 | Marshall et al. |
| 2016/0237478 | A1 | 8/2016 | Jewett et al. |
| 2016/0250612 | A1 | 9/2016 | Oldenburg et al. |
| 2016/0266041 | A1 | 9/2016 | Livingston |
| 2016/0291004 | A1 | 10/2016 | Sijbers et al. |
| 2016/0319341 | A1 | 11/2016 | Dressman et al. |
| 2017/0000899 | A1 | 1/2017 | Pridgen et al. |
| 2017/0022546 | A1 | 1/2017 | Bashir et al. |
| 2017/0023593 | A1 | 1/2017 | Van Roosmalen |
| 2017/0067889 | A1 | 3/2017 | Tamir |
| 2017/0113223 | A1 | 4/2017 | Immink et al. |
| 2017/0153248 | A1 | 6/2017 | Goix et al. |
| 2024/0269673 | A1 | 8/2024 | Gonzales et al. |
| 2025/0128255 | A1 | 4/2025 | Wang et al. |
| 2025/0128260 | A1 | 4/2025 | Seo et al. |
| 2025/0325981 | A1 | 10/2025 | Matsuda et al. |

FOREIGN PATENT DOCUMENTS

| | | | | |
|---|---|---|---|---|
| DE | 102012213044 | B3 | 1/2014 | |
| DE | 102014224664 | B3 | 10/2015 | |
| EP | 2629095 | A1 | 8/2013 | |
| EP | 2437048 | B1 | 1/2016 | |
| EP | 3523027 | A1 | 8/2019 | |
| EP | 2691178 | B1 | 2/2020 | |
| EP | 3632563 | A1 | 4/2020 | |
| EP | 3877086 | A2 | 9/2021 | |
| EP | 4140583 | A1 | 3/2023 | |
| EP | 4357789 | A1 | 4/2024 | |
| EP | 4549017 | A1 | 5/2025 | |
| EP | 4627333 | A2 | 10/2025 | |
| EP | 4665501 | A2 | 12/2025 | |
| WO | 2007008550 | A1 | 1/2007 | |
| WO | WO-2012030870 | A1 * | 3/2012 | ....... G01N 33/54313 |
| WO | 2012137122 | A1 | 10/2012 | |
| WO | WO 2013/189502 | A1 | 12/2013 | |
| WO | WO 2018/023088 | A1 | 2/2018 | |
| WO | WO 2018/119437 | A2 | 6/2018 | |
| WO | WO 2018/140719 | A1 | 8/2018 | |
| WO | WO 2022/029732 | A1 | 2/2022 | |
| WO | 2024194145 | A1 | 9/2024 | |
| WO | 2025032002 | A1 | 2/2025 | |

OTHER PUBLICATIONS

Glass et al., A combination of labeled an unlabeled antibody enables self-calibration and reduction of sample matrix effects in immunoassay, Analytical Biochemistry, 331, (2004), p. 68-76. (Year: 2004).*

Safarik et al., Magnetic techniques for the isolation and purification of proteins and peptides, BioMagnetic Research and Technology, 2(7), (2004), 17 pages. (Year: 2004).*

International Search Report, PCT Application No. PCT/US18/15440, dated Apr. 17, 2018, 4 pages.

International Search Report of PCT Application No. PCT/IB2021/057294, dated Feb. 10, 2020. (5 pages).

Oh, et al., "A three-linelateral flow assay strip for the measurement of C-reactive protein covering a broad physiological concentration range in human sera", Biosensors and Bioelectronics, vol. 61, pp. 285-289. (2014).

International Search Report and Written Opinion issued in corresponding International Patent Application No. PCT/IB2021/057294, dated Oct. 25, 2021.

Wang, et al., "Rapid Sensitive, and Simultaneous Detection of Three Foodhome Pathogens Using Magnetic Nanobead-Based Immunoseparation and Quantum Dot-Based Multiplex Immunoassay," J. of Food Protection, 2011, vol. 74, No. 12, pp. 2039-2047.

Godino, Neus et al., "Comprehensive integration of homogeneous bioassays via centrifugo-pneumatic cascading." Lab Chip, 13:685-694 (2013).

Madou, M.J., Lee, L.J., Daunert, S. et al., "Design and Fabrication of CD-like Microfluidic Platforms for Diagnostics: Microfluidic Functions." Biomedical Microdevices 3, 245-254 (2001).

Noroozi, Zahra et al., "A multiplexed immunoassay system based upon reciprocating centrifugal microfluidics." Review of Scientific Instruments 82:064303 (2011).

Schwemmer, F. et al., "Centrifugo-pneumatic multi-liquid aliquoting—parallel aliquoting and combination of multiple liquids in centrifugal microfluidics." Lab Chip, 15:3250-3258 (2015).

(56) References Cited

OTHER PUBLICATIONS

Strohmeier, O. et al., “Centrifugal microfluidic platforms: advanced unit operations and applications.” Chem. Soc. Rev., 44:6187-6229 (2015).

* cited by examiner

MULTIPLEXED ANALYTE DETECTION

CROSS-REFERENCE TO RELATED APPLICATIONS

This application is a 371 National Stage application of PCT/IB2021/057294, filed Aug. 6, 2021, which claims the benefit of and priority to U.S. Provisional Patent Application No. 63/063,028, filed Aug. 7, 2020 entitled "MULTIPLEXED ANALYTE DETECTION," which is incorporated by reference herein in its entirety.

TECHNICAL FIELD

The present invention relates to, inter alia, methods to detect presence, absence, or amount of a plurality of analytes in a biological sample.

SEQUENCE LISTING

The instant application contains a Sequence Listing that has been submitted in ASCII format via EFS-Web and is hereby incorporated by reference in its entirety. Said ASCII copy, created on Aug. 6, 2021, is named 124436-5011_Sequence_Listing_ST25.txt, and is 8, 192 bytes in size.

BACKGROUND

Medicine, biomedical research, and other fields rely on detection, identification, and quantification of various target analytes, including proteins, small molecules, bacteria, whole cells, viruses, and other analytes in biological and other types of samples. Reliable tests are required to detect a diverse range of targets, for diagnosing diseases and conditions, monitoring and assessing treatment progression, and for various other purposes of clinical and non-clinical applications.

Traditional methods for analyte detection involve assays such as, for example, enzyme-linked immunosorbent assays (ELISA), mass spectrometry, flow cytometry, and high pressure liquid chromatography (HPLC). Each of the existing approaches has its advantages and limitations. For example, ELISA assay, which is widely used in many fields, including for antibody detection, can be time-consuming as it includes multiple laborious procedures. Also, parameters of the ELISA assays may be highly variable, and ELISA may not be sufficiency sensitive which may compromise detection quality.

Moreover, biological samples and different other types of samples are often complex such that they include multiple target analytes. Multiplexed assays are desired in various biomedical, clinical, epidemiological, forensics, and other applications. However, conventional immunoassays, having long processing times and other drawbacks, are typically not well suited for simultaneous detection of more than one analyte. For example, ELISA can detect only one analyte in a sample. Moreover, in existing immunoassay systems, a volume of a sample required for analysis typically scales linearly with the number of analytes being detected. It can thus be challenging to detect multiple analytes.

Accordingly, there exists a need for reliable, accurate, and time-efficient diagnostic tests for comprehensive analysis of a sample, including for detection of multiple analytes in the sample.

SUMMARY

Accordingly, in various aspects, the present invention provides methods for detecting the presence, absence, or amount of a plurality of analytes in a biological sample, and kits to effect such methods. The methods allow for multiplexed detection of multiple analytes in a sample. By tagging each analyte with a reporter particle having a certain property (e.g., capable of generating a signal of a specific color), the described approach can be used for simultaneous detection of multiple analytes in the same sample. The method scales efficiently as a function of a number of analytes, such that a volume of the sample does not need to be increased for the detection of multiple analytes. Also, the method has improved sensitivity, specificity, reduced background noise, and increased signal-to-noise ratio.

In various aspects, the present invention provides a method for detecting the presence, absence, or amount of a plurality of analytes in a biological sample which can be obtained from a subject. The method comprises (a) contacting the sample with at least one magnetic conjugate comprising a magnetic particle and a plurality of capture moieties coupled to the magnetic particle and each configured to bind a corresponding analyte of the plurality of analytes; (b) contacting the magnetic conjugate with a plurality of reporter binding moieties each having a corresponding tag bound thereto, each reporter binding moiety being configured to bind a corresponding analyte of the plurality of analytes; (c) contacting the magnetic conjugate with a plurality of reporters each having a corresponding tag binding partner bound that is configured to bind a corresponding tag thereby optionally associating a reporter binding moiety with a corresponding reporter, wherein each reporter is configured to generate a corresponding different signal; (d) applying a magnetic field to separate the at least one magnetic conjugate, optionally having associated therewith an analyte of the plurality of analytes and the corresponding reporter binding moiety associated with the corresponding reporter bound thereto via a tag-tag binding partner interaction; and (e) detecting the presence, absence, or level of each analyte of the plurality of analytes based on detection of a signal generated by each of the reporters.

In aspects there is provided, a multiplexed method for detecting the presence, absence, or amount of a plurality of analytes in a biological sample, the method comprising: (a) contacting the sample with at least one magnetic conjugate comprising a magnetic particle and a plurality of capture moieties coupled to the magnetic particle and each configured to bind a corresponding analyte of the plurality of analytes; (b) contacting the magnetic conjugate with a plurality of reporter binding moieties each having a corresponding tag bound thereto, the tag comprising desthiobiotin and each reporter binding moiety being configured to bind a corresponding analyte of the plurality of analytes; (c) contacting the magnetic conjugate with a plurality of reporters each having a corresponding tag binding partner that is configured to bind a corresponding tag thereby associating a reporter binding moiety with a corresponding reporter, wherein the tag binding partner comprises streptavidin and each reporter is configured to generate a corresponding different signal; (d) applying a magnetic field to separate the magnetic conjugate, having associated therewith an analyte of the plurality of analytes and the corresponding reporter binding moiety associated with the corresponding reporter bound thereto via a tag-tag binding partner interaction; and (e) detecting the presence, absence, or level of each analyte of the plurality of analytes based on detection of a signal generated by each of the reporters, wherein: the reporter binding moiety has a first oligonucleotide bound thereto, and the reporter has a second oligonucleotide bound thereto, wherein the second oligonucleotide is configured to hybridize to the first oligonucleotide when the tag interacts with the tag binding partner, thereby associating the reporter binding moiety with the reporter; and each of the first oligonucleotide and the second oligonucleotide has a length of about 50 nucleotides or less.

In some embodiments, the method for detecting the presence, absence, or amount of a plurality of analytes in a biological sample comprises (a) contacting the sample with at least one magnetic conjugate comprising a magnetic particle and a plurality of capture moieties coupled to the magnetic particle and each configured to bind a corresponding analyte of the plurality of analytes; (b) contacting the sample with a plurality of reporter binding moieties each having a corresponding tag bound thereto, each reporter binding moiety being configured to bind a corresponding analyte of the plurality of analytes; (c) contacting the sample with a plurality of reporters each having a corresponding tag binding partner bound thereto such that the tag binding partner binds a corresponding tag thereby associating a reporter binding moiety bound to the tag with a corresponding reporter, wherein each reporter is configured to generate a corresponding different signal; (d) separating each analyte of the plurality of analytes that has the corresponding magnetic particle and the corresponding reporter binding moiety associated with the corresponding reporter bound thereto via a tag-tag binding partner interaction from the sample by applying a magnetic field; and (e) detecting the presence, absence, or level of each analyte of the plurality of analytes based on detection of a signal generated by each of the reporters.

In some embodiments, a magnetic pulldown and wash (resuspension) are performed between the steps (b) and (c), which can remove excess reporter binding moieties that can be present in a reaction mixture with the sample.

In some embodiments, tag-tag binding partner pairs are orthogonal, such that a tag binds only a corresponding tag binding partner, and vice versa. Thus, for detection of certain analytes in a sample, tag-tag binding partner pairs can be selected such that no interaction can occur between tag and tag binding partners from different pairs. In other words, each tag-tag binding partner pair is selected to be specific to a particular analyte of the plurality of analytes to be detected.

Various tags and corresponding tag binding partners can be used in accordance with embodiments of the present disclosure. In some embodiments, the tag comprises biotin and the tag binding partner comprises streptavidin, or the tag comprises fluorescein isothiocyanate (FITC) and the tag binding partner comprises anti-FITC antibody, or the tag comprises dinitrophenol (DNP) and the tag binding partner comprises anti-DNP antibody, or the tag comprises digoxigenin (DIG) and the tag binding partner comprises anti-DIG antibody, or the tag comprises Etag (GAPVPYPDPLEPR (SEQ ID NO: 1) and the tag binding partner comprises an anti-Etag antibody, or the tag comprises FLAG (DYKDDDDK (SEQ ID NO: 2)) and the tag binding partner comprises an anti-FLAG antibody, or the tag comprises Myc (EQKLISEEDL (SEQ ID NO: 3) and the tag binding partner comprises an anti-Myc antibody, or the tag comprises HA (YPYDVPDYA (SEQ ID NO: 4) and the tag binding partner comprises an anti-HA antibody, or the tag comprises SNAP and the tag binding partner comprises a benzylguanine derivative, or the tag comprises "CLIP" and the tag binding partner comprises a benzylcytosine derivative.

In some embodiments, the tag-tag binding partner interaction is facilitated by use of oligonucleotides that can hybridize to one another, if there is complementarity, when a reporter binding moiety associates with a corresponding reporter via the tag-tag binding partner interaction. In such embodiments, oligonucleotide pairs are selected such that they are unique for detection of a certain analyte from a plurality of analyte, thus allowing simulations detection of multiple analytes in a sample. In these embodiments, the same tags and tag binding partners can be used for detection of analytes of the plurality of analytes. The tag may be a tag with a short binding half-life (which can also be referred to as a low affinity tag or a tag with a high off rate). Such a tag can be, without limitation, desthiobiotin (or its derivative or analogue) configured to bind a corresponding tag binding partner, such as, e.g. avidin (e.g., without limitation, streptavidin). Any other tags and tag binding partners can be used.

Accordingly, in some embodiments, the reporter binding moiety has a first oligonucleotide bound thereto, and the reporter has a second oligonucleotide bound thereto, wherein the second oligonucleotide is configured to hybridize to the first oligonucleotide when the tag interacts with the tag binding partner, thereby associating the reporter binding moiety with the reporter.

The first oligonucleotide and the second oligonucleotide can be fully or partially complementary to one another. In some embodiments, the first and second oligonucleotides can be fully complementary to one another. In some embodiments, the first and second oligonucleotides may not be perfectly complementary, while they may still be able to hybridize to one another.

In some embodiments, each of the first oligonucleotide and the second oligonucleotide has a length of about 50 nucleotides or less.

In some embodiments, a capture moiety of the plurality of capture moieties of the at least one magnetic conjugate comprises an antibody configured to bind a corresponding analyte of the plurality of analytes. All or at least some of the plurality of capture moieties coupled to the magnetic particle can be antibodies. Various analytes can simultaneously be detected using such capture moieties (e.g., hCG, PSA, TSH, and CRP in the blood).

In some embodiments, a capture moiety of the plurality of capture moieties of the at least one magnetic conjugate comprises a first antibody configured to bind the corresponding analyte of the plurality of analytes, and wherein a reporter binding moiety comprises a second antibody configured to bind the corresponding analyte. In such embodiments, the plurality of analytes can comprise a plurality of antibodies, and a capture moiety of the at least one magnetic conjugate can comprise an antigen configured to bind a corresponding antibody. In some embodiments, a reporter binding moiety of the plurality of reporter binding moieties comprises a secondary antibody configured to bind the antigen. The method may indicate whether the subject is producing or not producing antibodies directed against an antigen. In some embodiments, the method may provide an amount of antibodies in the sample.

In some embodiments, the reporter molecule is a metal core and a silica shell or the reporter; wherein the silica shell is optionally impregnated with a plurality of quantum dots; and wherein the metal core optionally comprises gold. In some embodiments, the reporter comprises a plurality of quantum dots, a single quantum dot, organic dye, upconverting phosphors, and other types.

In embodiments, each reporter of the plurality of reporters is capable of generating a corresponding signal that has at least one property that is different from a property of a signal generated by another reporter of the plurality of reporters.

In embodiments, the method allows simultaneously detecting of at least four analytes, or at least six analytes, or any other number of analytes.

In embodiments, the method allows simultaneously detecting of at least 2 analytes, or at least 3 analytes, or at least 4 analytes, or at least 5 analytes, or at least 6 analytes, or at least 7 analytes, or at least 8 analytes, or at least 9 analytes, or at least 10 analytes.

In embodiments, the method allows simultaneously detecting of about 2 analytes, or about 3 analytes, or about 4 analytes, or about 5 analytes, or about 6 analytes, or about 7 analytes, or about 8 analytes, or about 9 analytes, or about 10 analytes.

In various aspects, the present invention provides a kit suitable for the method of any of the embodiments disclosed herein. The kit may comprise the at least one magnetic conjugate, the plurality of reporter binding moieties, and the plurality of reporters.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

Any aspect or embodiment disclosed herein can be combined with any other aspect or embodiment as disclosed herein.

BRIEF DESCRIPTION OF THE DRAWINGS

FIG. 1A illustrates magnetic particles, each coupled to a corresponding capture moiety and an analyte of interest. FIG. 1B shows that the analytes of FIG. 1A each associate with a reporter binding moiety having a tag bound thereto. FIG. 1C illustrates final, detectable complexes that are each formed when a corresponding reporter, having a tag binding partner bound, binds with a corresponding reporter binding moiety of FIG. 1A via a tag-tag binding partner interaction. Each of the reporters can generate a signal of a different color. FIG. 1D illustrates that a magnetic field can be applied such that the complexes of FIG. 1C are separated from the sample.

FIG. 1E illustrates that detection of different signals generated by the reporters of the complexes of FIG. 1D allows detecting the corresponding analytes.

FIG. 2A depicts a reporter binding moiety having a tag (e.g. desthiobiotin) and a first oligonucleotide bound thereto, and a reporter (orange) having a tag binding partner (e.g. streptavidin) and a second oligonucleotide bound thereto. FIG. 2B shows that, when the first oligonucleotide and the second oligonucleotide are complementary to one another, they hybridize to one another to form a stable structure, thereby associating the reporter binding moiety with the reporter.

FIG. 3A depicts a reporter binding moiety having a tag (e.g. desthiobiotin) and a first oligonucleotide bound thereto, and a reporter (orange) having a tag binding partner (e.g. streptavidin) and a second oligonucleotide bound thereto. FIG. 3B shows that, when the first oligonucleotide and the second oligonucleotide are not complementary to one another, the tag-tag binding partner interaction dissociates and the reporter binding moiety does not become associated with the reporter.

DETAILED DESCRIPTION

Figure 1A:
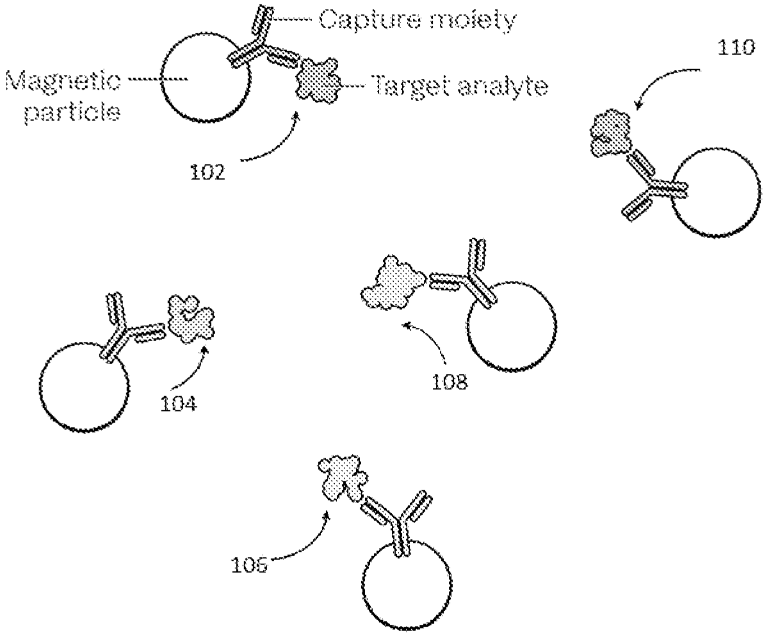
FIGS. 1A to 1E illustrate an example of a method of detection of a plurality of analytes in a sample in accordance with some embodiments of the present disclosure.

The present disclosure provides methods and systems that address the need for accurate detection of multiple analytes in biological samples.

In many scenarios related to diagnosing or treating a subject, it is desirable to detect multiple analytes simultaneously in the same sample, for a more comprehensive and more reliable analysis, and at a reduced time. Detection of more than one analyte in a sample can also be important in forensics, biometric identification, disease tracing, and in other various areas.

Traditional immunoassay systems can operate in parallel utilizing automated equipment. However, many conventional immunoassays suffer from long processing times (e.g., 3-6 hours), poor sensitivity (e.g., limit of detections (LoDs) in the picomolar—nanomolar range), and large sample volume requirements (e.g., hundreds of microliters). Moreover, a volume of a required sample may scale linearly with the number of analytes being probed. For example, if a system requires about 100 μl sample for detection of one analyte, then it will require about 500 μl of a sample volume for detection of five analytes. The requirement for a large sample volume can be a limitation in many circumstances. Detection of multiple analytes in a multiplexed manner therefore remains to be a challenge.

Accordingly, embodiments of the present disclosure provide a multiplexed immunoassay that is characterized by a low background across different samples (e.g., bodily fluids), high sensitivity, and reduced total assay time. Also, the multiplexing is achieved by utilizing identical or similar procedures across different analytes and assay types, which allows reducing costs, and improving speed, reliability, and reproducibility of the analysis.

In embodiments, the described multiplexed immunoassay employs magnetic particles and a reporter system for fluorescent detection. Each analyte being detected can be tagged with a different reporter particle, and the described method therefore scales more efficiently as a function of number of analytes, as compared to traditional approaches. For example, the same volume of a sample can be required for detection of one, two, three, four, five, six, or more than six analytes. The reporter particle can be capable of generating a signal of a certain color (e.g., a reporter particle that comprises one or more quantum dots), or it can have having another property that distinguishes that reporter particle from other reporter particles tagging other analytes. Non-limiting examples of other properties include surface charge, charge density, scattering properties, as well as other properties of reporter particles. In some embodiments, reporter particles can be associated with (e.g. coated with) nucleic acid-based barcodes, in which case polymerase chain reaction (PCR) can be used to detect the reporter by detecting the nucleic acid-based barcodes. The orthogonal reporter particles can allow simultaneously measuring more than one separate analyte in a small sample volume (e.g., a 1 μl sample).

In various aspects, the present invention provides a method for detecting the presence, absence, or amount of a plurality of analytes in a biological sample. The method comprises (a) contacting the sample with at least one magnetic conjugate comprising a magnetic particle and a plurality of capture moieties coupled to the magnetic particle and each configured to bind a corresponding analyte of the plurality of analytes; (b) contacting the magnetic conjugate with a plurality of reporter binding moieties each having a corresponding tag bound thereto, each reporter binding moiety being configured to bind a corresponding analyte of the plurality of analytes; (c) contacting the magnetic conjugate with a plurality of reporters each having a corresponding tag binding partner that is configured to bind a corresponding tag thereby optionally associating a reporter binding moiety with a corresponding reporter, wherein each reporter is configured to generate a corresponding different signal; (d) applying a magnetic field to separate the at least one magnetic conjugate, optionally having associated therewith an analyte of the plurality of analytes and the corresponding reporter binding moiety associated with the corresponding reporter bound thereto via a tag-tag binding partner interaction; and (e) detecting the presence, absence, or level of each analyte of the plurality of analytes based on detection of a signal generated by each of the reporters.

In embodiments, the magnetic conjugate will have associated therewith an analyte of the plurality of analytes (the analyte having the corresponding reporter binding moiety associated with the corresponding reporter, bound thereto via a tag-tag binding partner interaction) when the analyte is present in the sample. When the analyte is not present in the sample, the magnetic conjugate will not be associated with an analyte. In addition, in some embodiments, when a magnetic particle has a plurality of capture moieties configured to bind corresponding different analytes, one or more of the capture moieties may have a corresponding analyte abound thereto, while one or more other capture moieties may not be bound to analyte(s) because of absence of corresponding analytes from the sample.

In some embodiments, a method for detecting the presence, absence, or amount of a plurality of analytes in a biological sample comprises (a) contacting the sample with at least one magnetic conjugate comprising a magnetic particle and a plurality of capture moieties coupled to the magnetic particle and each configured to bind a corresponding analyte of the plurality of analytes; (b) contacting the sample with a plurality of reporter binding moieties each having a corresponding tag bound thereto, each reporter binding moiety being configured to bind a corresponding analyte of the plurality of analytes; (c) contacting the sample with a plurality of reporters each having a corresponding tag binding partner bound thereto such that the tag binding partner binds a corresponding tag thereby associating a reporter binding moiety bound to the tag with a corresponding reporter, wherein each reporter is configured to generate a corresponding different signal; (d) separating each analyte of the plurality of analytes that has the corresponding magnetic particle and the corresponding reporter binding moiety associated with the corresponding reporter bound thereto via a tag-tag binding partner interaction from the sample by applying a magnetic field; and (e) detecting the presence, absence, or level of each analyte of the plurality of analytes based on detection of a signal generated by each of the reporters.

In some embodiments, a magnetic pulldown and wash (resuspension) are performed, separately or simultaneously, between the steps (b) and (c), which can remove excess reporter binding moieties that can be present in a reaction mixture including the sample. After the excess of the reporter binding moieties is removed, the sample can be resuspended with a plurality of reporters which, in some embodiments, can have a concentration substantially lower than a concentration of the reporter binding moieties.

Various tags and corresponding tag binding partners can be used in accordance with embodiments of the present disclosure. In some embodiments, the tag comprises biotin and the tag binding partner comprises avidin, or the tag comprises fluorescein isothiocyanate (FITC) and the tag binding partner comprises anti-FITC antibody, or the tag comprises dinitrophenol (DNP) and the tag binding partner comprises anti-DNP antibody, or the tag comprises digoxigenin (DIG) and the tag binding partner comprises anti-DIG antibody, or the tag comprises Etag and the tag binding partner comprises an anti-Etag antibody (GAPVPYPDPLEPR (SEQ ID NO: 1)), or the tag comprises FLAG and the tag binding partner comprises an anti-FLAG antibody (DYKDDDDK (SEQ ID NO: 2), or the tag comprises Myc and the tag binding partner comprises an anti-Myc antibody (EQKLISEEDL (SEQ ID NO: 3)), or the tag comprises HA and the tag binding partner comprises an anti-HA antibody (YPYDVPDYA (SEQ ID NO: 4), or the tag comprises SNAP and the tag binding partner comprises a benzylguanine derivative, or the tag comprises "CLIP" and the tag binding partner comprises a benzylcytosine derivative.

Various tags can be used in methods and kits in accordance with embodiments of the present disclosure. The tags can be, e.g., peptide tags, covalent peptide tags, and protein tags.

Non-limiting examples of peptide tags comprise ALFA-tag, a de novo designed helical peptide tag (SRLEEELRRRLTE (SEQ ID NO: 5) for biochemical and microscopy applications. The tag is recognized by a repertoire of single-domain antibodies; AviTag, a peptide allowing biotinylation by the enzyme BirA and so the protein can be isolated by streptavidin (GLNDIFEAQKIEWHE (SEQ ID NO: 6); C-tag, a peptide that binds to a single-domain camelid antibody developed through phage display (EPEA (SEQ ID NO: 7); Calmodulin-tag, a peptide bound by the protein calmodulin (KRRWKKNFIAVSAANRFKKISSSGAL (SEQ ID NO: 8); polyglutamate tag, a peptide binding efficiently to anion-exchange resin such as Mono-Q (EEEEEE (SEQ ID NO: 9)); polyarginine tag, a peptide binding efficiently to cation-exchange resin (from 5 to 9 consecutive R); E-tag, a peptide recognized by an antibody (GAPVPYPDPLEPR (SEQ ID NO: 1); FLAG-tag, a peptide recognized by an antibody (DYKDDDDK (SEQ ID NO: 2)); HA-tag, a peptide from hemagglutinin recognized by an antibody (YPYDVPDYA (SEQ ID NO: 4)); His-tag, 5-10 histidines bound by a nickel or cobalt chelate (HHHHHH (SEQ ID NO: 10)); Myc-tag, a peptide derived from c-myc recognized by an antibody (EQKLISEEDL (SEQ ID NO: 3)); NE-tag, an 18-amino-acid synthetic peptide (TKENPRSNQEESYDDNES (SEQ ID NO: 11)) recognized by a monoclonal IgG1 antibody; Rho1D4-tag, refers to the last 9 amino acids of the intracellular C-terminus of bovine rhodopsin (TETSQVAPA (SEQ ID NO: 12)); S-tag, a peptide derived from Ribonuclease A (KETAAAKFERQHMDS (SEQ ID NO: 13)); SBP-tag, a peptide which binds to streptavidin (MDEKTTGWRGGHVVEGLAGELEQLRARLEHHPQGQREP (SEQ ID NO: 14)); Spot-tag, a peptide recognized by a nanobody (PDRVRAVSHWSS (SEQ ID NO: 15)) for immunoprecipitation, affinity purification, immunofluorescence and super resolution microscopy; Strep-tag, a peptide which binds to streptavidin or the modified streptavidin called streptactin (Strep-tag II: WSHPQFEK (SEQ ID NO: 16); T7-tag, an epitope tag derived from the T7 major capsid protein of the T7 gene (MASMTGGQQMG (SEQ ID NO: 17)); TC tag, a tetracysteine tag that is recognized by FIASH and ReAsH biarsenical compounds (CCPGCC (SEQ ID NO: 18); Ty tag (EVHTNQDPLD (SEQ ID NO: 19); V5 tag, a peptide recognized by an antibody (GKPIPNPLLGLDST (SEQ ID NO: 20); VSV-tag, a peptide recognized by an antibody (YTDIEMNRLGK); and Xpress tag (DLYDDDDK (SEQ ID NO: 21)).

Non-limiting examples of covalent peptide tags comprise Isopeptag, a peptide which binds covalently to pilin-C protein (TDKDMTITFTNKKDAE (SEQ ID NO: 22)); SpyTag, a peptide which binds covalently to SpyCatcher protein (AHIVMVDAYKPTK (SEQ ID NO: 23)); SnoopTag, a peptide which binds covalently to SnoopCatcher protein (KLGDIEFIKVNK (SEQ ID NO: 24)); DogTag, a peptide which covalently binds to SnoopTagJr, mediated by SnoopLigase (DIPATYEFTDGKHYITNEPIPPK (SEQ ID NO: 25); SdyTag, a peptide which binds covalently to SdyCatcher protein (DPIVMIDNDKPIT (SEQ ID NO: 26); and SdyTag/SdyCatcher has a kinetic-dependent cross-reactivity with SpyTag/SpyCatcher.

Non-limiting examples of protein tags comprise BCCP (Biotin Carboxyl Carrier Protein), a protein domain biotinylated by BirA enabling recognition by streptavidin; Glutathione-S-transferase-tag, a protein which binds to immobilized glutathione; Green fluorescent protein-tag, a protein which is spontaneously fluorescent and can be bound by nanobodies; HaloTag, a mutated bacterial haloalkane dehalogenase that covalently attaches to haloalkane substrates; SNAP-tag, a mutated eukaryotic DNA methyltransferase that covalently attaches to benzylguanine derivatives; CLIP-tag, a mutated eukaryotic DNA methyltransferase that covalently attaches to benzylcytosine derivatives; HUH-tag, a sequence-specific single-stranded DNA binding protein that covalently binds to its target sequence; Maltose binding protein-tag, a protein which binds to amylose agarose; Nus-tag; Thioredoxin-tag; Fc-tag, derived from immunoglobulin Fc domain, allow dimerization and solubilization; and Carbohydrate Recognition Domain or “CRDSAT-tag”, a protein which binds to lactose agarose or Sepharose.

In some embodiments, tags and corresponding tag binding partners are selected for detection of a plurality of analytes in a sample such that a different tag-tag binding partner pair is used for detection of each analyte of the multiple analytes. Thus, a tag bound to a reporter binding moiety will only interact with a corresponding tag binding partner, specific for this tag in the particular multiplexing reaction. In this way, the tag-tag binding partner pair specific to a certain analyte is used to associate a reporter binding moiety (bound to the tag) with a reporter (bound to the tag binding partner), thereby allowing detecting the analyte by measuring a property of a reporter (e.g., without limitation, color, intensity of fluorescence, etc.).

In some embodiments, reporters that can generate signals of different colors can be used. Different suitable technologies can be employed. For example, in some embodiments, reporter molecules can be beads or other types of reporters that are coated with organic fluorescent dyes. In some embodiments, reporter molecules are fluorophore-encoded microbeads, e.g. beads encoded different dyes.

In some embodiments, the reporter may be a fluorescent reporter, a phosphorescent reporter, or a colorimetric reporter such as a colored particle that may be configured to measure absorbance or scattering of light (or, for example, the presence/absence of a certain color by colorimetric analysis).

In some embodiments, the reporter comprises one or more quantum dots. The quantum dots can be configured to emit signal of certain colors (wavelength and frequency). As known, atoms can emit light having a color that depends on what the identity atom, i.e. different atoms can generate different colors of light. This occurs because the energy levels in atoms have set values, i.e. they are quantized. Quantum dots produce light in a similar way, because the electrons and holes constrained inside them give them similarly discrete, quantized energy levels.

The energy levels in quantum dots depend on the size of a quantum dot. For example, quantum dots made from the same material will produce different colors of light depending on their size. The bigger the quantum dot, the longer wavelengths (and the lower frequencies) it produces. Quantum dots of a smaller size produce shorter wavelengths (and higher frequencies). Thus, in use, large quantum dots generate red light and small dots generate blue light, whereas intermediate-sized dots producing green light, as well as spectrum of other colors. Emission spectra of quantum dots can be well distinguishable from one another.

In some embodiments, a light source can be used to simultaneously excite a plurality of reporters (e.g., quantum dots capable of producing different colors).

In embodiments, detection of a reporter allows detecting presence, absence, or amount of a respective target analyte, associated with that reporter in an assay in accordance with embodiments of the present disclosure. In embodiments, detection of the reporters allows detecting analyte(s) in the sample depending on whether or not one or more of the multiple analytes being detected are present in the sample.

In some embodiments, detection of multiple colors results in detection of multiple analytes in the sample. In some embodiments, detection of multiple colors results in detection of all of the multiple analytes being detected in the sample. In some embodiments, detection of some colors results in detection of some but not all of the multiple analytes being detected in the sample.

In embodiments, the reporters can be detected using, for example, fluorescence microscopy, scanning electron microscope (SEM), or another technique.

In some embodiments, the same tags and tag binding partners, where a relatively weak interaction occurs between a tag and a tag binding partner, are used for detection of a plurality of analytes in a sample. In such embodiments, oligonucleotide pairs, specific to each analyte, are employed for selective interaction and subsequent binding between a reporter capture moiety (associated with a tag) and a reporter (associated with a tag binding partner). In these embodiments, the tag may be a tag with a short binding half-life, which can also be referred to as a low affinity tag or a tag with a high off-rate. The low affinity tag can be, without limitation, a tag comprising desthiobiotin (or its derivatives or equivalents), which is the biotin analog that binds to avidin (the streptavidin homologue) with a dissociation constant that is $10^2$-$10^4$ fold weaker than that of biotin. Desthiobiotin binds to streptavidin with a similar low affinity. A tag binding partner can comprise, without limitation, avidin (e.g. streptavidin), or another tag binding partner capable of forming an interaction with the tag with a relatively high dissociation constant ($K_d$). For example, the $K_d$ can be at least about 10 times, at least about 50 times, at least about 100 times, or at least about 1000 times, or at least about 10000 times greater than a $K_d$ of biotin/streptavidin association.

The interaction between a reporter binding moiety and a reporter occurs when respective tag and tag binding partner come together to create a low affinity binding therebetween. The binding occurs quickly, but it is not stable (high on-rate ($K_{on}$) and high off-rate ($K_{off}$)). In these embodiments, however, the interaction between the reporter binding moiety and the reporter is facilitated by use of oligonucleotides that can hybridize to one another thereby associating the reporter binding moiety with the reporter. In such embodiments, oligonucleotide pairs are selected such that they are unique for detection of a certain analyte from a plurality of analytes.

Accordingly, in some embodiments, the reporter binding moiety has a first oligonucleotide bound thereto, and the reporter has a second oligonucleotide bound thereto, wherein the second oligonucleotide is configured to hybridize to the first oligonucleotide when the tag interacts with the tag binding partner, thereby associating the reporter binding moiety with the reporter. The tag is a low affinity tag, e.g. without limitation, desthiobiotin or its derivatives or equivalents, or any other low affinity tag. The tag binding partner comprises, e.g. without limitation, avidin (e.g. streptavidin), or another tag binding partner capable of forming a weak binding with a corresponding tag. The low affinity tag binds quickly but weakly with the corresponding partner, with the high on-rate and high off-rate, and stable binding between the reporter binding moiety and the reporter is created only if there is complementarity between the first and second oligonucleotides. The interaction between the first and second oligonucleotides is high affinity, and a reporter conjugate forms when the oligonucleotides are complementary to one another and the reporter and the reporter binding moiety thus come together. If there is no complementarity between the first and second oligonucleotides, the strength of the tag-tag binding partner binding falls off rapidly, and the reporter binding moiety does not become associated with the reporter.

The first oligonucleotide and the second oligonucleotide can be fully or partially complementary to one another. For each analyte of a plurality of analytes to be detected, the first and second oligonucleotides can be selected such that they hybridize to one another, and they do not hybridize to first and second oligonucleotides employed for detection of another analyte of the plurality of analytes.

In some embodiments, each of the first oligonucleotide and the second oligonucleotide has a length of about 50 nucleotides or less. For example, the first and second oligonucleotides can have a length of about 10 nucleotides, or about 20 nucleotides, or about 30 nucleotides, or about 40 nucleotides, or about 50 nucleotides, or about 60 nucleotides.

The methods in accordance with embodiments of the present disclosure allow detection of various analytes in a sample. In some embodiments, an analyte comprises an antigen.

In some embodiments, a capture moiety of the plurality of capture moieties of the at least one magnetic conjugate comprises an antibody configured to bind a corresponding analyte of the plurality of analytes. All or at least some of the plurality of capture moieties coupled to the magnetic particle can be antibodies. Various analytes can simultaneously be detected using such capture moieties (e.g., hCG, PSA, TSH, and CRP in the blood).

In some embodiments, a capture moiety of the plurality of capture moieties of the at least one magnetic conjugate comprises a first antibody configured to bind the corresponding analyte of the plurality of analytes, wherein a reporter binding moiety comprises a second antibody configured to bind the corresponding analyte. In such embodiments, the plurality of analytes can comprise a plurality of antibodies, and a capture moiety of the at least one magnetic conjugate can comprise an antigen configured to bind a corresponding antibody. In some embodiments, a reporter binding moiety of the plurality of reporter binding moieties comprises a secondary antibody configured to bind the antigen. The method may indicate whether the subject is producing or not producing antibodies directed against an antigen. In some embodiments, the method may provide an amount of antibodies in the sample. In some embodiments, the capture moieties and the reporter binding moiety bind different portions of the analyte. In some embodiments, the capture moieties and the reporter binding moieties are different. In some embodiments, the capture moieties and the reporter binding moieties bind to different antigens or epitopes.

Various reporters can be used in embodiments of the present disclosure. In some embodiments, the reporter molecule is a metal core and a silica shell or the reporter; wherein the silica shell is optionally impregnated with a plurality of quantum dots; and wherein the metal core optionally comprises gold. In some embodiments, the reporter comprises a plurality of quantum dots, a single quantum dot, organic dye, upconverting phosphors, and other types.

In embodiments, the method employs a relatively low amount of a plurality of quantum dots, e.g. about 400 pM or less, or about 300 PM or less, or about 200 pM or less, or about 100 pM or less, or about 50 pM or less, or about 10 PM or less, e.g. about 400 pM, or about 300 pM, or about 200 pM or less, or about 100 pM, or about 50 pM, or about 10 pM.

In some embodiments, the reporter is a fluorescent reporter, a phosphorescent reporter, or a colorimetric reporter.

In embodiments of the present disclosure, use of a reporter binding moiety that has a tag bound thereto and that is configured to associate with a reporter via a tag binding partner that can interact with a tag (e.g. via an antigen-antibody interaction), allows substantially increasing the speed of the detection. A concentration of the reporter binding moiety can be substantially greater than a concentration of the reporter—e.g., the concentration of the reporter binding moiety can be in a nanomolar range, whereas the concentration of the reporter can be in a picomolar range. In some embodiments, a concentration of the reporter binding moiety can be about 10-6 M, or about 10-7 M, or about 10-8 M. In some embodiments, a concentration of the reporter binding moiety can be at least about 10-6 M, or at least about 10-7 M, or at least about 10-8 M. The concentration of the reporter can be less than about 10-11 M, or no greater than 10-11 M. Thus, the kinetics of the creation of a detectable complex (i.e. the complex comprising the analyte bound to a magnetic particle and to a reporter) is dramatically improved, in some cases by 1000 times faster. Also, the proportion of bound, detectable analytes, as compared to undetected analytes present in the sample, can be improved significantly, up to 100% in some case. This further improves a signal-to-noise ratio, reduces background noise, and improves specificity and sensitivity of the multiplexing detection.

Accordingly, in some embodiments, a concentration of the reporter binding moiety is greater than a concentration of the reporter, optionally at least 5 times greater, or at least 10 times greater, or at least 100 times greater, or at least 1000 times greater.

In some embodiments, the concentration of the reporter binding moiety or concentrations of the plurality of reporter binding moieties (e.g. at least 2, or at least 3, or at least 4, or at least 5, or at least 6, or at least 10 of the report binding moieties) is about 1000 times greater than the concentration of the reporter or concentrations of the plurality of reporters (e.g. at least 2, or at least 3, or at least 4, or at least 5, or at least 6, or at least 10 of the reporters).

In some embodiments, the concentration of the reporter or concentrations of the plurality of reporters (e.g. at least 2, or at least 3, or at least 4, or at least 5, or at least 6, or at least 10 of the reporters) is in a picomolar range. For example, the concentration of the reporter or concentrations of the plurality of reporters (e.g. at least 2, or at least 3, or at least 4, or at least 5, or at least 6, or at least 10 of the reporters) may be less than about 300 pM. In some embodiments, the concentration of the reporter or concentrations of the plurality of reporters (e.g. at least 2, or at least 3, or at least 4, or at least 5, or at least 6, or at least 10 of the reporters) is from about 10 PM to about 140 pM, or from about 40 PM to about 140 pM, from about 40 PM to about 100 pM, or from about 60 pM to about 100 pM, or from about 80 pM to about 100 pM, or from about 100 pM to about 140 pM. In some embodiments, the concentration of the reporter or concentrations of the plurality of reporters (e.g. at least 2, or at least 3, or at least 4, or at least 5, or at least 6, or at least 10 of the reporters) is about 20 pM, or about 40 pM, or about 60 pM, or about 80 pM, or about 100 pM. In some embodiments, the concentration of the reporter or concentrations of the plurality of reporters (e.g. at least 2, or at least 3, or at least 4, or at least 5, or at least 6, or at least 10 of the reporters) is about 120 pM.

In some embodiments, the concentration of the reporter binding moiety or concentrations of the plurality of reporter binding moieties (e.g. at least 2, or at least 3, or at least 4, or at least 5, or at least 6, or at least 10 of the report binding moieties) is in a nanomolar range. For example, the concentration of the reporter binding moiety or concentrations of the plurality of reporter binding moieties (e.g. at least 2, or at least 3, or at least 4, or at least 5, or at least 6, or at least 10 of the report binding moieties) may be greater than about 1 nm. In some embodiments, the concentration of the reporter binding moiety or concentrations of the plurality of reporter binding moieties (e.g. at least 2, or at least 3, or at least 4, or at least 5, or at least 6, or at least 10 of the report binding moieties) is from about 1 nm to about 60 nM, or from about 1 nm to about 50 nM, or from about 1 nm to about 40 nM, or from about 1 nm to about 30 nM, or from about 1 nm to about 20 nM, or from about 1 nm to about 15 nM, or from about 1 nm to about 10 nM, or from about 1 nm to about 5 nM. In some embodiments, the concentration of the reporter binding moiety or concentrations of the plurality of reporter binding moieties (e.g. at least 2, or at least 3, or at least 4, or at least 5, or at least 6, or at least 10 of the report binding moieties) is from about 100 nm to about 700 nM, e.g., about 100 nM, or about 200 nM, or about 300 nM, or about 400 nM, or about 500 nM, or about 600 nM, or about 600 nM.

In some embodiments, the concentration of the reporter binding moiety or concentrations of the plurality of reporter binding moieties (e.g. at least 2, or at least 3, or at least 4, or at least 5, or at least 6, or at least 10 of the report binding moieties) ranges from about 1 nM to about 10 nM, and the concentration of the reporter ranges from about 15 PM to about 25 pM. In some embodiments, the concentration of the reporter binding moiety or concentrations of the plurality of reporter binding moieties (e.g. at least 2, or at least 3, or at least 4, or at least 5, or at least 6, or at least 10 of the report binding moieties) is about 5 nM and the concentration of the reporter is about 20 pM.

In embodiments, each reporter of the plurality of reporters is capable of generating a corresponding signal that has at least one property that is different from a property of a signal generated by another reporter of the plurality of reporters. In embodiments, the method allows simultaneously detecting at least four analytes, or at least six analytes, or any other number of analytes. In some embodiments, the method allows detecting at least 2, at least 3, at least 4, at least 5, at least 6, at least 7, at least 8, at least 9, or at least 10 analytes, or more than 10 analytes. In some embodiments, the method allows detecting 2, 3, 4, 5, 6, 7, 8, 9, or 10 analytes, or more than 10 analytes.

Various analytes can be detected using the methods in accordance with embodiments of the present disclosure. In some embodiments, the analyte is or comprises a protein biomarker. In some embodiments, the analyte is or comprises one or more of human chorionic gonadotropin (hCG), luteinizing hormone (LH)/Lutropin, prostate specific antigen (PSA), herpes simplex virus (HSV) antibodies, estrone-3-glucuronide (E3G), bacteria, hemoglobin A1C, C-reactive protein (CRP), an inflammation biomarker, troponin, lyme disease antigen, lyme disease antibodies, an LDL biomarker, an HDL biomarker, a total cholesterol biomarker, thyroid stimulating hormone, a hepatitis C virus biomarker, a rhino virus biomarker, an influenza virus biomarker, a liver function biomarker, estrogen, progesterone, lactic acid, and combinations thereof (e.g. at least 2, or at least 3, or at least 4, or at least 5, or at least 6, or at least 10 of the foregoing). In some embodiments, the analyte additionally or alternatively comprises one or more of N-terminal (NT)-pro hormone BNP (NT-proBNP), C-reactive protein (CRP), D-Dimer, Vitamin-D, Vitamin B12, T3, T4, Thyroid-stimulating hormone (TSH), Parathyroid hormone (PTH), Follicle stimulating hormone (FSH), Ferritin, luteinizing hormone (LH), human chorionic gonadotropin (hCG), Progesterone, Estradiol, Testosterone, Prostate-specific antigen (PSA), and Homocysteine, and combinations thereof (e.g. at least 2, or at least 3, or at least 4, or at least 5, or at least 6, or at least 10 of the foregoing).

In some embodiments, the protein biomarker is selected from the group consisting of human chorionic gonadotropin (hCG), luteinizing hormone (LH)/Lutropin, prostate specific antigen (PSA), herpes simplex virus (HSV) antibodies, estrone-3-glucuronide (E3G), bacteria, hemoglobin A1C, C-reactive protein, an inflammation biomarker, troponin, lyme disease antigen, lyme disease antibodies, an LDL biomarker, an HDL biomarker, a total cholesterol biomarker, thyroid stimulating hormone, a hepatitis C virus biomarker, a rhino virus biomarker, an influenza virus biomarker, a liver function biomarker, estrogen, progesterone, lactic acid, and combinations thereof (e.g. at least 2, or at least 3, or at least 4, or at least 5, or at least 6, or at least 10 of the foregoing).

In embodiments, non-limiting examples of a sample include whole blood, plasma, serum, bile, saliva, urine, tears, perspiration, cerebrospinal fluid (CSF), semen, mucus, sputum, menstrual blood, menstrual fluid, vaginal mucus, amniotic fluid, synovial fluid, breast milk, ear wax, preejaculate, lochia, Rheum, lymph, pus, and combinations thereof. In some embodiments, the sample is whole blood, plasma, serum, or urine.

In some embodiments, the sample has a volume of about 1 microliter. In some embodiments, the sample has a volume of smaller than 1 microliter. In some embodiments, the sample has a volume of about 2 microliters, or about 3 microliters, or about 4 microliters, or about 5 microliters.

In some embodiments, e.g. in which the detected analytes comprise antibodies, the method further comprises a step of pre-treating the sample with a magnetic conjugate comprising a magnetic particle and a moiety configured to bind contaminant antibodies and/or non-antibody moieties. In some embodiments, the contaminant antibodies are not directed against the antigen configured to bind the corresponding antibody or are ineffective at generating an immune response against the antigen configured to bind the corresponding antibody. In some embodiments, wherein the pre-treating reduces or eliminates one or more of: (a) heterophile antibodies; (b) antibodies that non-specifically interact with the magnetic particle; and (c) non-antibody moieties that non-specifically interact with the magnetic particle.

In some embodiments, the method is suitable for point-of-care usage. In some embodiments, the method is suitable for field usage and/or the method is suitable for home usage.

In some embodiments, the methods are compatible with the World Health Organization's ASSURED (affordable, sensitive, specific, user-friendly, rapid and robust, equipment-free, and deliverable) criteria.

In some embodiments, the method is substantially free of false positives. In some embodiments, the method is substantially free of false negatives.

In some embodiments, the method provides better sensitivity and specificity than a solid phase immunoassay method, a bead-based flow cytometry, or a lateral flow immunochromatographic assay.

In some embodiments, the method provides better sensitivity and specificity than a method using a bead-based flow cytometry-based assays, optionally bead-based, flow cytometry-based assays. In some embodiments, the method provides better sensitivity and specificity than a method using a lateral flow immunochromatographic assay.

In some embodiments, the method provides nanomolar, or picomolar, or femtomolar scale sensitivity.

In various aspects, the present invention provides a kit suitable for the method of any of the embodiments disclosed herein. The kit may comprise the at least one magnetic conjugate, the plurality of reporter binding moieties, and the plurality of reporters.

In embodiments, the methods in accordance with the present disclosure employ a nanoparticle-based immunoassay configured to detect the presence, absence, or level of the antibody by detecting the reporter. In some embodiments, the immunoassay can be implemented similar to assays described in PCT/US2018/015440 (published as WO2018140719) or as a variation or combination of those assays, the disclosure of which is incorporated by reference herein in its entirety.

Immunoassays

Methods described herein include methods for detecting the presence, absence, or amount of a plurality of analytes in a biological sample.

FIGS. 1A to 1E illustrate an example of a method of detection of a plurality of target analytes in sample. FIG. 1A illustrates magnetic particles, each coupled to a corresponding capture moiety and an analyte of interest ("target analyte"). In this example, five analytes of interest 102, 104, 106, 108, and 110 are being detected, as shown for illustration purposes only.

Figure 1B:
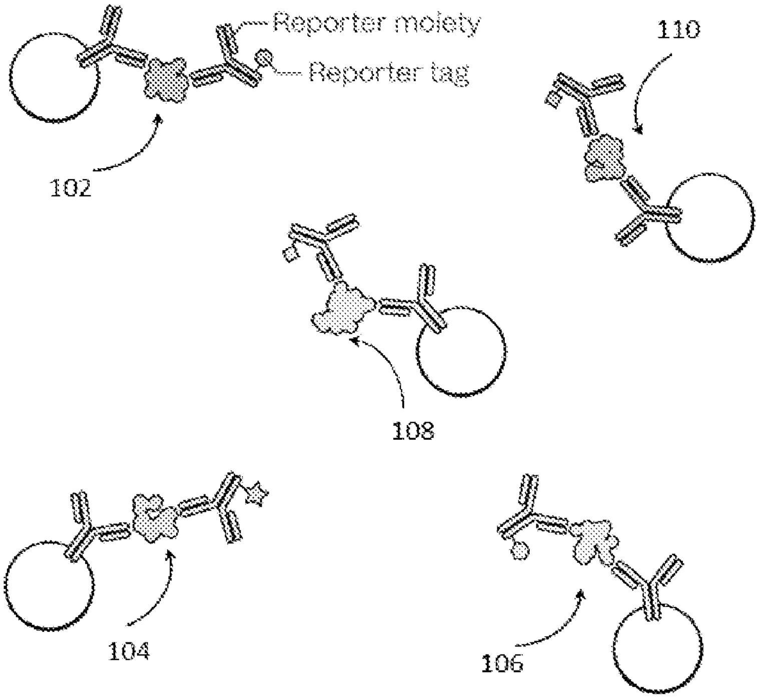
Figure 1C:
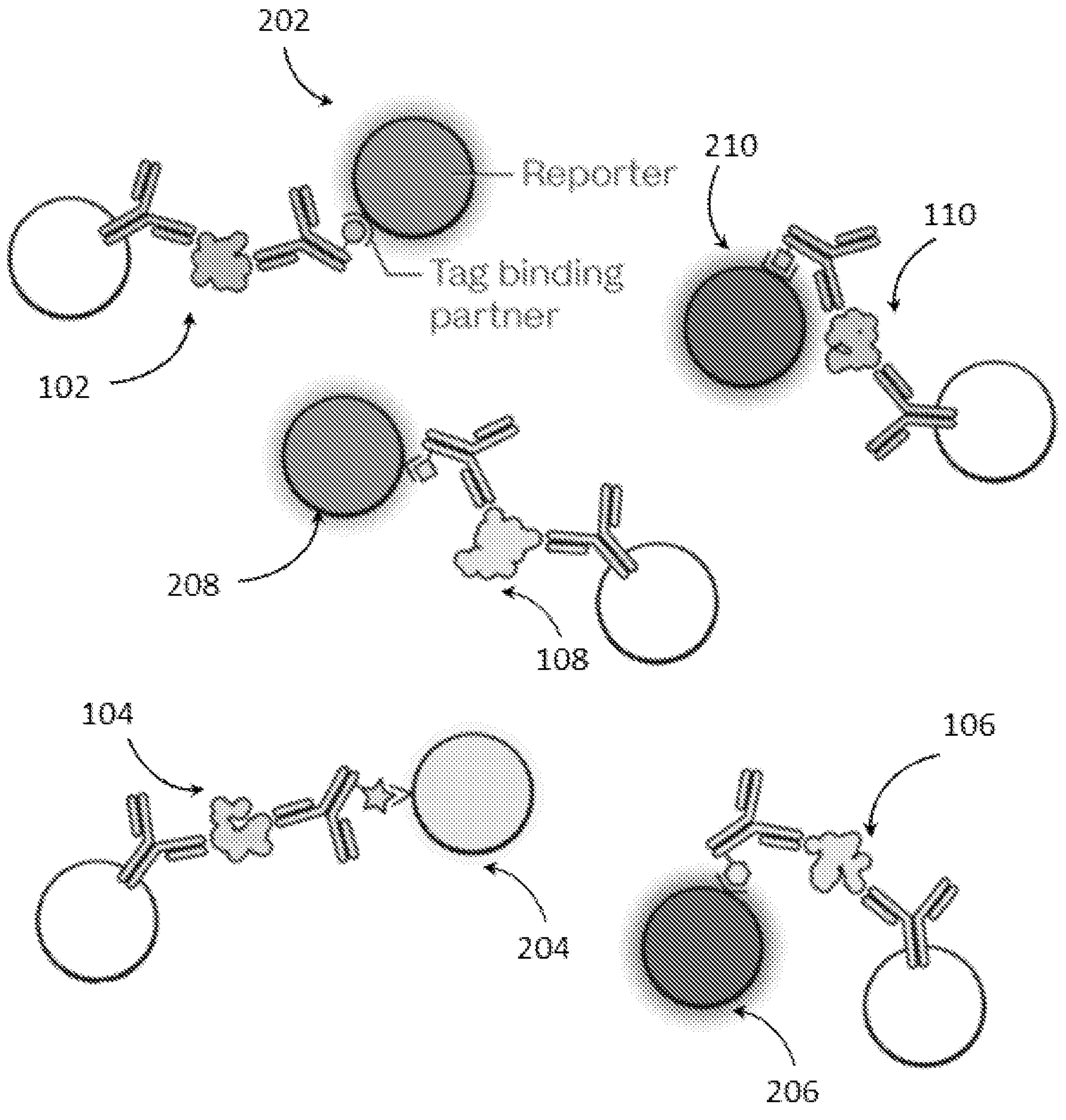
Figure 1D:
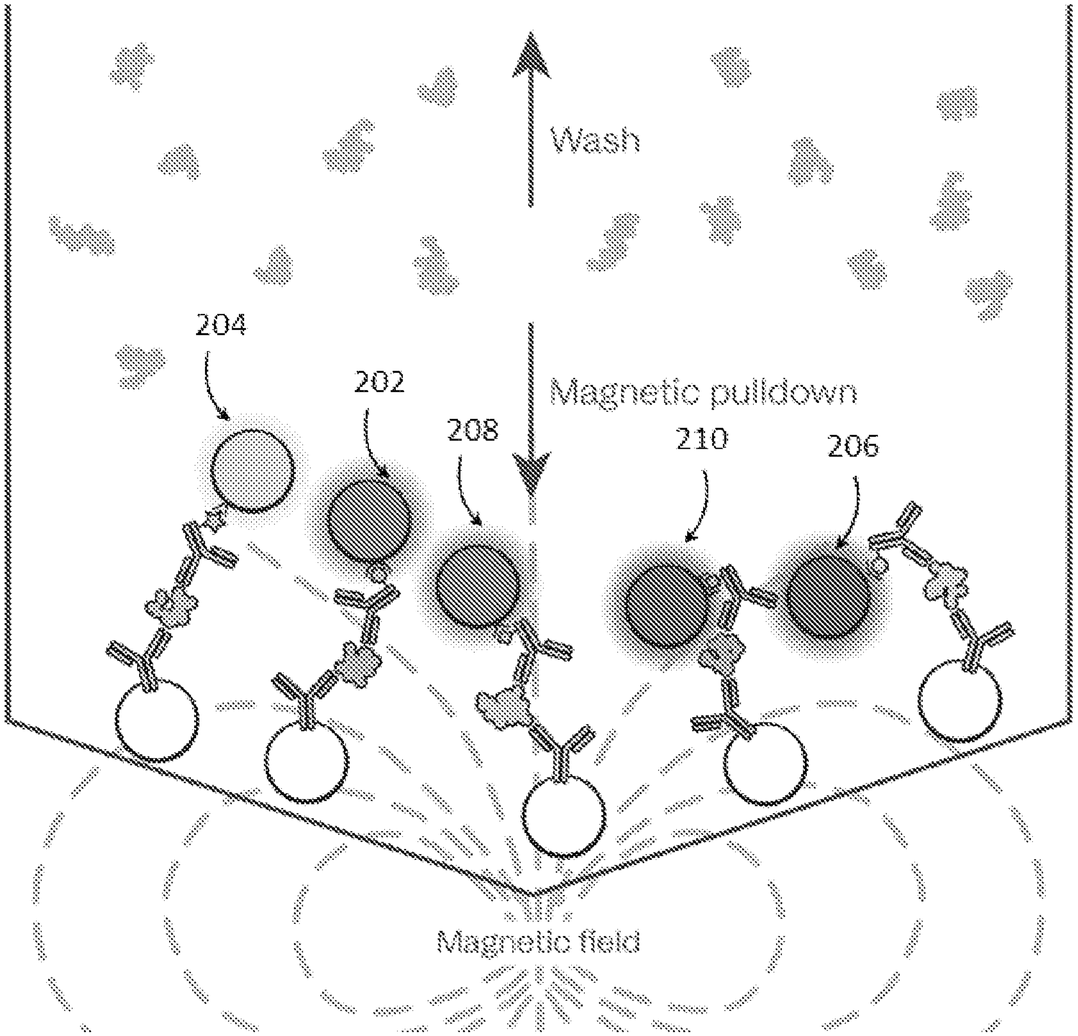

FIG. 1B shows that the analytes 102, 104, 106, 108, and 110 of FIG. 1A can each associate with a reporter binding moiety ("Reporter moiety") with a tag ("Reporter tag") bound thereto. In FIG. 1C, the final complexes are formed with a corresponding reporter 202, 204, 206, 208, and 210 bound to each reporter binding moiety that is, in turn, bound to an analyte from the analytes 102, 104, 106, 108, and 110. Each of the reporters 202, 204, 206, 208, and 210 can generate a signal of a different color—e.g., orange (202), yellow (204), red (206), green (208), and blue (210). For example, each reporter can comprise one or more quantum dots of a different size. Each reporter has a tag binding partner bound thereto that is configured to bind with a corresponding tag and thereby associate the reporter with the reporter binding moiety bound to that tag via a tag-tag binding partner interaction. FIG. 1D illustrates that a magnetic field can be applied such that the complexes are separated from the sample. The rest of the sample can then be washed away ("Wash").

Figure 1E:
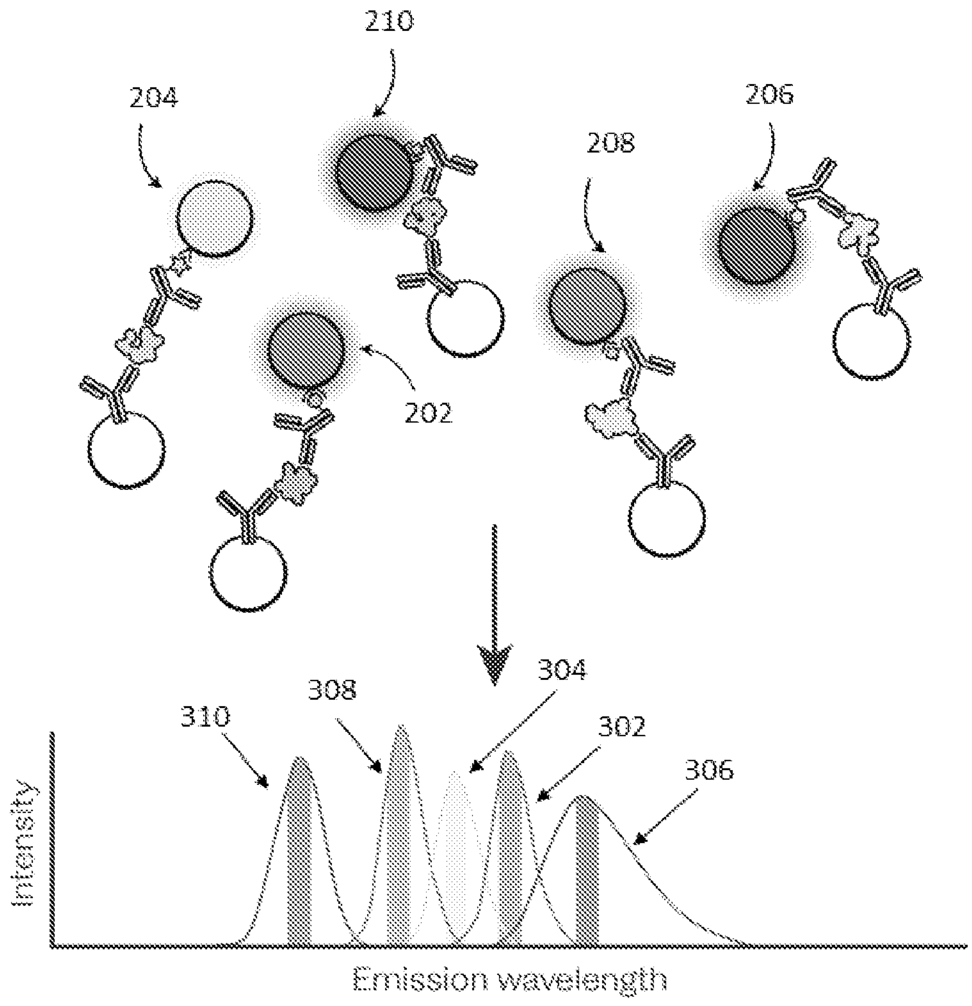

FIG. 1E illustrates that detection of different signals generated by the reporters 202, 204, 206, 208, and 210 allows detecting the corresponding antibodies associated with those reporters. In this example, the reporters 202, 204, 206, 208, and 210 generate signals (spectra) 302, 304, 306, 308, and 310, respectively, which have different colors. In this way, the plurality of analytes in the sample are detected. It should be appreciated however that, depending on whether or not an analyte is present in a sample, a respective signal may or may not be detected as a result of detection of reporters.

In some embodiments, for formation of a final detectable complex for detection of each analyte of a plurality of analytes, a reporter binding moiety can be associate with a corresponding reporter via an interaction between respective oligonucleotide bound to the reporter binding moiety and the reporter.

In embodiments, the method detects the presence of one or a plurality of analytes and the absence of one or a plurality of analytes. In embodiments, the method detects the concentration or level of a plurality of analytes.

Figure 2A:
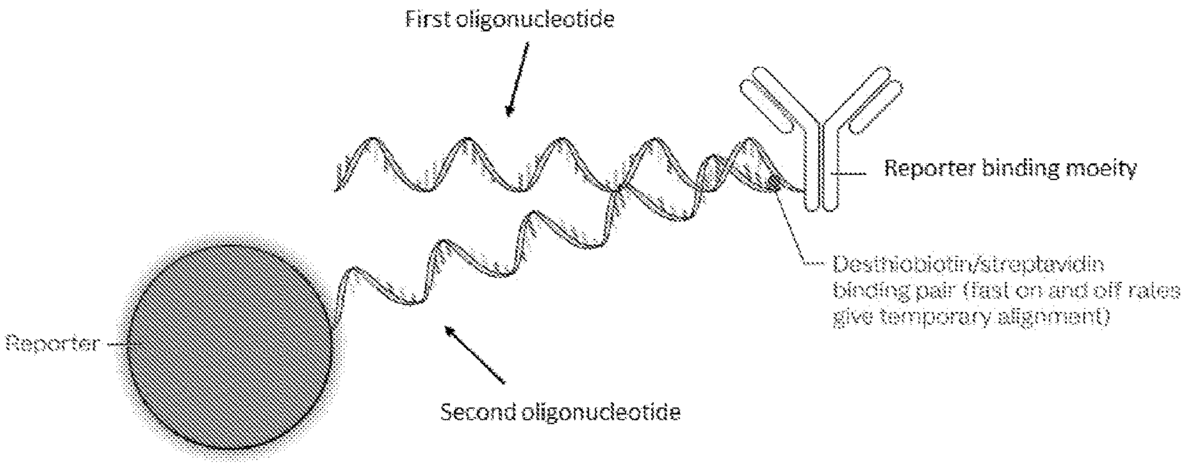
FIGS. 2A and 2B illustrate an example of a method of detection of a plurality of analytes in a sample in accordance with some embodiments of the present disclosure.
Figure 2B:
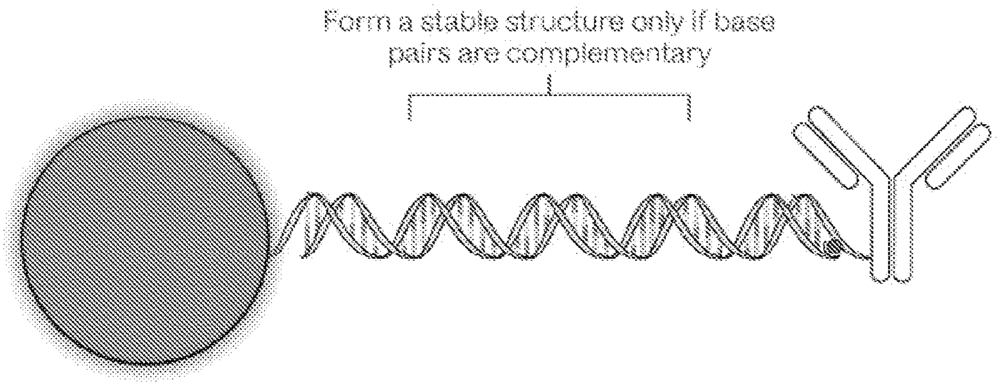

FIGS. 2A and 2B illustrate an example of a method of detection of a plurality of analytes in a sample in accordance with some embodiments of the present disclosure. FIG. 2A depicts a reporter binding moiety (having an antibody-like shape, by way of example only) having a tag (e.g. desthiobiotin) and a first oligonucleotide bound thereto, and a reporter (orange circle) having a tag binding partner (e.g. streptavidin) and a second oligonucleotide bound thereto. In the example of FIGS. 2A and 2B, the first and second oligonucleotides are complementary to one another.

As shown in FIG. 2A, the reporter binding moiety is associated with the tag such that the tag is positioned in proximity to the reporter binding moiety. The tag can be coupled to the first oligonucleotide. In some embodiments, the tag can be otherwise associated with the reporter binding moiety. As also shown in FIG. 2A, the reporter is associated with the tag binding partner (e.g. streptavidin) such that the tag binding partner is positioned at the end of the second oligonucleotide that is opposite to the end coupled to the reporter. In this way when the tag and the tag binding partner associate with one another, with the fast on-rate and fast off-rate, the first and second oligonucleotides are positioned for possible alignment, if there is complementarity therebetween. Thus, FIG. 2B shows that, because the first oligonucleotide and the second oligonucleotide of FIG. 2A are complementary to one another, they hybridize to one another to form a stable structure, thereby associating the reporter binding moiety with the reporter.

It should be appreciated that the complementarity between the first and second oligonucleotides sufficient for hybridization can be less than 100% complementarity. For example, in some embodiments, the first and second oligonucleotides can be at least about 60%, at least about 70%, or at least about 80%, or at least about 90%, or at least about 95%, or at least about 98%, or at least about 99%, or 100% complementary to one another.

In some embodiments, the first and second oligonucleotides are perfectly complementary to one another. In some embodiments, the first and second oligonucleotides are not perfectly complementary to one another. Perfect complementarity may not be required for hybridization between the first and second oligonucleotides.

Figure 3A:
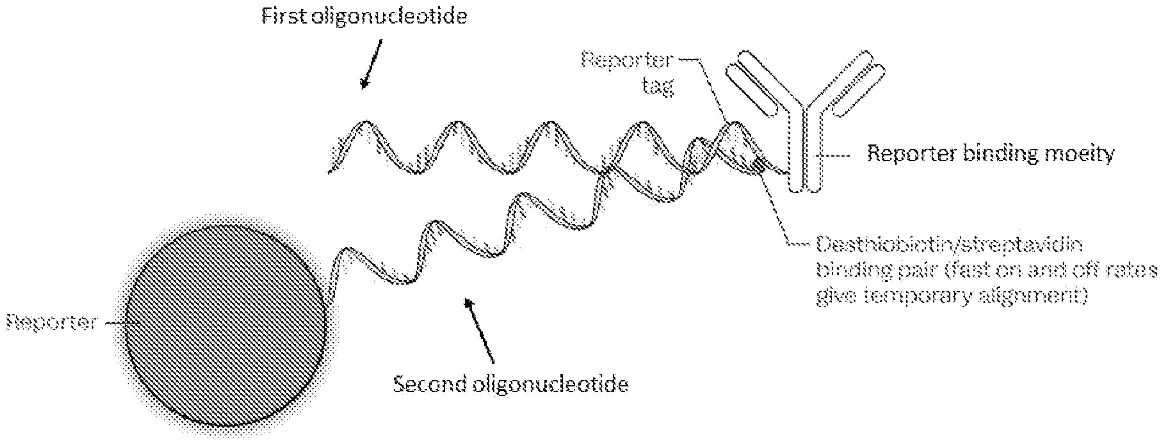
FIGS. 3A and 3B illustrate another example of a method of detection of a plurality of analytes in a sample in accordance with some embodiments of the present disclosure.
Figure 3B:
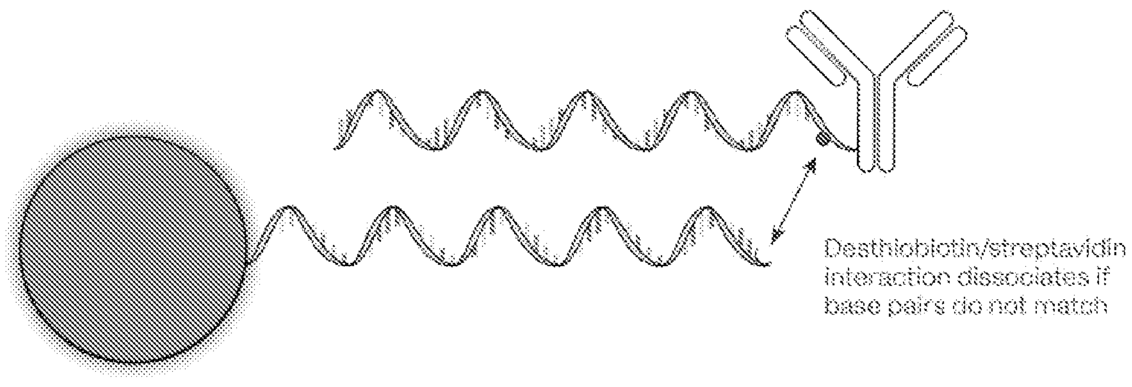

FIGS. 3A and 3B illustrate another example of a method of detection of a plurality of analytes in a sample in accordance with some embodiments of the present disclosure. FIG. 3A depicts a reporter binding moiety having a tag (e.g. desthiobiotin) and a first oligonucleotide bound thereto, and a reporter (orange) having a tag binding partner (e.g. streptavidin) and a second oligonucleotide bound thereto. In the example of FIGS. 3A and 3B, the first and second oligonucleotides are not complementary to one another. FIG. 3B shows that, when the first oligonucleotide and the second oligonucleotide are not complementary to one another (or not sufficiency complementary), the tag-tag binding partner interaction dissociates and the reporter binding moiety does not become associated with the reporter.

In certain embodiments, the methods described herein encompass a sandwich method, a separate addition method, a competitive method, a tertiary (three binding event) method, a whole cell assay method, or combinations thereof.

For example, the sandwich method, for detection of multiple analytes, described above, may be well suited for processing small fluid sample volumes. The separate addition method described herein may enable processing of larger fluid volumes, with improved sensitivity. The competitive assay method may be useful, e.g., for assaying analytes in scenarios in which a matched pair of a capture moiety and a corresponding reporter binding moiety that would bind to an analyte simultaneously is not available. The tertiary assay method may encompass three binding events to enhance the kinetics of a system employed for the present method.

In some embodiments, a method for detecting the presence, absence, or amount of a plurality of analytes in a biological sample can comprise a sandwich method, separate addition method, and/or competitive assay method, or any combinations thereof.

In embodiments, the methods described herein employ immunoassays such as nanoparticle-based immunoassays configured to perform the present detection of the presence, absence, or amount of a plurality of analytes in a biological sample. The nanoparticle-based immunoassays can be implemented as part of a multiplex testing platform, which can be a portable system. The system can be in the form of a kit including all the components necessary to perform the present detection.

In some embodiments of the method implemented in accordance with a sandwich immunoassay method, a reporter can be, e.g., one or more gold core particles with a silica shell impregnated with 100-600 quantum dots (nanoComposix, San Diego, CA). In some embodiments, the reporter comprises one or more quantum dots, or another nanoparticle.

In some embodiments, a reporter can be used that is a bright reporter (i.e. generates a signal of high quality), has high surface area, and remains colloidally stable during the analysis. For example, in some embodiments, such reporter can be a particle that includes a large number (e.g., several hundred) of highly fluorescent quantum dots providing up to about 300× optical amplification of the signal.

The sandwich immunoassay involves detection of whether a complex is formed comprising at least one magnetic conjugate, an analyte of interest, and a reporter binding moiety associated with a corresponding reporter bound thereto via a tag-tag binding partner interaction. In embodiments, the at least one magnetic conjugate comprises a magnetic particle and a plurality of capture moieties coupled to the magnetic particle and each configured to bind a corresponding analyte of the plurality of analytes. In this way, multiple analytes can be detected in a sample using the same magnetic particle. The assay can include one magnetic conjugate comprising a magnetic particle and a plurality of capture moieties coupled to the magnetic particle and each configured to bind a corresponding analyte of the plurality of analytes. In some embodiments, the assay includes more than one magnetic conjugate. Furthermore, in some embodiments, the assay can include various types of magnetic conjugates, including at least one magnetic conjugate comprising a magnetic particle and a plurality of capture moieties coupled to that magnetic particle, and at least one magnetic conjugate comprising a magnetic particle and one capture moiety coupled to that magnetic particle.

The complex ("sandwich") is formed only in the presence of the analyte. When the analyte is present, the resulting complex can be attracted by a magnet and provides an optical signal that increases its intensity as the analyte concentration increases.

The sandwich complex cannot form in absence of the analyte, because the reporter binding moiety/reporter system does not bind with the magnetic conjugate. When not associated with a magnetic particle, the reporter is washed away and does not generate a signal when the sample is analyzed.

In some embodiments of the sandwich immunoassay method, a magnetic conjugate (comprising a magnetic particle and a plurality of capture moieties coupled to the magnetic particle and each configured to bind a corresponding analyte of the plurality of analytes), a plurality of reporter binding moieties (each having a corresponding tag bound thereto, each reporter binding moiety being configured to bind a corresponding analyte of the plurality of analytes), and a plurality of reporters (each having a corresponding tag binding partner bound thereto such that the tag binding partner binds a corresponding tag thereby associating a reporter binding moiety bound to the tag with a corresponding reporter, wherein each reporter is configured to generate a corresponding different signal) may be added to an analysis chamber and mixed with a biological sample including one or more analytes of interest. A magnetic field may be applied (a "pulldown") by a magnet to separate the analytes from the sample. The pulldown can be performed by applying a magnetic field to the sample (with other ingredients added) for a certain time period (e.g., about 1 minute, or about 2 minutes, or about 3 minutes, or about 4 minutes, or about 5 minutes, or about 6 minutes, or about 7 minutes). In some embodiments, the magnetic field is applied for about 5 minutes. It should be appreciated however that the magnetic field can be applied to the sample for any suitable duration of time.

If the reporter is a fluorescence signal reporter (e.g., an organic dye, nanomaterial, or conjugated polymer), light may then be transmitted through at least a portion of the analysis chamber to cause the reporter to fluoresce. Such fluorescence may be detected by a suitable detector. In embodiments, reporters associated with corresponding different analytes can generate signals of different colors, such that detection of the reporters allows determining presence or amount of analytes of a plurality of analytes being detected. In the absence of the analyte(s) of interest, the reporter is not pulled down with the analytes and no fluorescence occurs.

In some embodiments, the method described herein may comprise: contacting the sample with a magnetic conjugate comprising a magnetic particle and a plurality of capture moieties coupled to the magnetic particle and each configured to bind a corresponding analyte of the plurality of analytes; (b) contacting the magnetic conjugate with a plurality of reporter binding moieties each having a corresponding tag bound thereto, each reporter binding moiety being configured to bind a corresponding analyte of the plurality of analytes; (c) contacting the magnetic conjugate with a plurality of reporters each having a corresponding tag binding partner that is configured to bind a corresponding tag thereby optionally associating a reporter binding moiety bound to the tag with a corresponding reporter, wherein each reporter is configured to generate a corresponding different signal; (d) applying a magnetic field to separate the magnetic conjugate, optionally having associated therewith an analyte of the plurality of analytes that has the corresponding reporter binding moiety associated with the corresponding reporter bound thereto via a tag-tag binding partner interaction; and (e) detecting the presence, absence, or level of each analyte of the plurality of analytes based on detection of a signal generated by each of the reporters.

In the above embodiment, a magnetic conjugate comprises a magnetic particle having a plurality of capture moieties coupled to the magnetic particle and each configured to bind a corresponding analyte of the plurality of analytes. In some embodiments, a magnetic conjugate comprises a magnetic particle having one capture moiety coupled thereto. Thus, in some embodiments, a method for detecting the presence, absence, or amount of a plurality of analytes in a biological sample comprises: (a) contacting the sample with a plurality of magnetic conjugates each comprising a magnetic particle and a capture moiety configured to bind a corresponding analyte of the plurality of analytes; (b) contacting the magnetic conjugates with a plurality of reporter binding moieties each having a corresponding tag bound thereto, each reporter binding moiety being configured to bind a corresponding analyte of the plurality of analytes; (c) contacting the magnetic conjugates with a plurality of reporters each having a corresponding tag binding partner bound thereto that is configured to bind a corresponding tag thereby optionally associating a reporter binding moiety bound to the tag with a corresponding reporter, wherein each reporter is configured to generate a corresponding different signal; (d) applying a magnetic field to separate the magnetic conjugates, each optionally having an analyte of the plurality of analytes that has the corresponding reporter binding moiety associated with the corresponding reporter bound thereto; and (e) detecting the presence, absence, or level of each analyte of the plurality of analytes based on detection of a signal generated by each of the reporters.

If the reporter is a fluorescence signal reporter, light may then be transmitted through at least a portion of an analysis chamber carrying the sample to cause the reporters to fluoresce, and the emitted fluorescence is measured by a suitable detector. The reporter can be detected using, e.g., a light source and a photodetector. In embodiments, the reporters, each bound to a respective analyte (if the analyte is present in the sample), generate corresponding signals of different properties, such as colors, and the method thus allows to discriminate between different analytes in the sample.

In some embodiments, additionally or alternatively to color, reporter particle properties such as surface charge, charge density, scattering properties, as well as other properties can be used to distinguish between different analytes being detected. In some embodiments, reporter particles can be associated with (e.g. coated with) nucleic acid-based barcodes, in which case polymerase chain reaction (PCR) can be used to detect the reporter by detecting the nucleic acid-based barcodes.

In embodiments, at least one magnetic conjugate (comprising a magnetic particle and a plurality of capture moieties coupled to the magnetic particle), a plurality of reporter binding moieties, and a plurality of reporters can be added to the analysis chamber simultaneously or at different times. Thus, in some embodiments, a magnetic conjugate, a plurality of reporter binding moieties, and a plurality of reporters may be added separately. Furthermore, in some embodiments, a plurality of reporter binding moieties and a plurality of reporters can be pre-bound to each other.

In some embodiments, an immunoassay method is a separate addition method, which can be used for processing larger volumes of samples (though small samples can be analyzed as well) and which allows concentrating an analyte of interest. This approach may allow detecting an analyte or multiple analytes simultaneously with improved sensitivity. In the separate addition method, at least one magnetic conjugate may be added to an analysis chamber and mixed with a sample which may or may not include an analyte of interest, or it can include some but not all of the plurality of analytes detected. A pulldown may be performed by activating a magnetic field (such that an analyte, if present, binds with a corresponding capture moiety of the magnetic conjugate), and a volume (e.g. a portion) of the sample may be removed. An additional volume of the sample may then be added. After (or, in some cases, before) the additional volume of the sample is added, the magnetic field may be deactivated and the magnetic conjugate may again be mixed with the sample. This process may be repeated a certain number of times to concentrate the analyte. After concentrating the analyte, the plurality of reporter binding moieties and the plurality of reporters may be added and mixed with the sample such that each reporter binding moiety binds a corresponding analyte of the plurality of analytes and a tag bound to the reporter binding moiety is bound to a corresponding tag binding partner that is, in turn, bound to a corresponding reporter, thereby the reporter binding moiety is associated with the corresponding reporter. A further magnetic pulldown may then be performed to separate the analytes which each (if present) are bound to a corresponding magnetic particle and a reporter (via a reporter binding moiety). If the reporter is a fluorescence signal reporter, light may then be transmitted through at least a portion of the analysis chamber to cause the reporter to fluoresce, and the emitted fluorescence is measured by a suitable detector. In the absence of analyte, the reporter will not be pulled down with the analyte and no fluorescence is detected.

In some embodiments, a competitive immunoassay method is performed, which can include two types of methods. Each of the methods can be used for simultaneous detection of a plurality of analytes in a sample.

The method of a first type of the competitive immunoassay method can be used in scenarios in which an analyte (e.g., without limitation, an antigen, antibody, cell, bacteria, virus, etc.) is too small for simultaneously binding with a corresponding capture moiety (coupled to a magnetic particle, as part of a magnetic conjugate) and a reporter binding moiety (which may or may not be coupled to a reporter, e.g., via a tag-tag binding partner interaction). This method may also be used where either of the capture moiety and the reporter binding moiety is not available. In this method, a magnetic conjugate may be added to an assay chamber and mixed with a biological sample that may or may not include an analyte of interest. A reporter-labeled second analyte (which is an analyte, different form the analyte off interest) configured to bind the magnetic conjugate in the absence of the analyte of interest) may then be added and mixed with the sample. When the analyte of interest is present in the sample, the reporter-labeled second analyte does not bind to the magnetic conjugate because a binding site of a capture moiety of the magnetic conjugate is occupied by the analyte of interest. However, if the analyte of interest is not present in the analyzed sample, the magnetic conjugate will bind to the reporter-labeled second analyte. A magnetic pulldown is performed to separate the analyte of interest (if present) from the sample. If the reporter is a fluorescence signal reporter, light may then be transmitted through at least a portion of the analysis chamber to cause the reporter to fluoresce, and the emitted fluorescence is measured by a suitable detector. In the absence of the analyte of interest, the reporter-labeled analyte will be pulled down with the magnetic conjugate and no fluorescence is detected.

Accordingly, in some embodiments (e.g., in which a first type of the competitive immunoassay method is implemented), the method described herein may include the steps of: (a) contacting a sample with a magnetic conjugate comprising a magnetic particle and at least one capture moiety configured to bind an analyte of interest the sample; (b) contacting the magnetic conjugate with a reporter-labeled second analyte configured to bind the magnetic conjugate in the absence of the analyte in the sample; (d) applying a magnetic field to the analysis chamber to pull down the magnetic conjugates, optionally having the analyte associated therewith; and (e) detecting the presence, absence, or level of the analyte by detecting the reporter with a light source and photodetector.

In a second type of the competitive immunoassay method, a magnetic particle (e.g., a magnetic bead) may be used with a second, competitive analyte bound thereto (e.g., an antigen, antibody, or another type). The second analyte can be different from an analyte of interest. The second analyte can be, e.g., an antigen configured to bind a reporter binding moiety that is configured to bind the analyte of interest. In the absence of the analyte of interest, the second analyte (bound to the magnetic particle) binds the reporter binding moiety associated with a reporter. The resulting complex can be attracted by a magnet and provides an optical signal that decreases in intensity as a concentration of the analyte of interest in the sample increases. If the analyte of interest is present in the sample, it blocks complex formation. In particular, when the analyte of interest is present in the sample, it can preemptively bind the reporter binding moiety, competing for the formation of the complete complex with the second analyte bound to the magnetic particle. For example, when the analyte of interest is an antigen, it binds the available binding sites on the reporter binding moiety (i.e. an antibody) thus preventing the binding of the second analyte (bound to the magnetic particle) to the reporter binding moiety (bound to a reporter). In this way, the antibody binding sites on the reporter binding moiety are occupied by the analyte of interest and the analyte of interest is thus competing for the formation of the complete complex. Accordingly, when a magnetic field is applied, the second analyte, which is bound to the magnetic particle and not bound to the reporter, is pulled down. The analyte of interest that is bound to the reporter via the reporter binding moiety (the reporter and the reporter binding moiety may interact via a tag-tag binding partner interaction) is washed away. Therefore, an optical signal generated by the reporter decreases in intensity as concentration of the analyte of interest increases.

In the second type of the competitive immunoassay method, the magnetic particle can be coupled to the second analyte (to form what is referred to as a magnetic particle-labeled analyte) before the assay is performed. In some embodiments, the method involves the use of a reporter conjugate comprising a reporter and a reporter binding moiety. The reporter conjugate is added to an analysis chamber comprising a biological sample, and mixed with the sample which may include an analyte of interest. The magnetic particles with the second analyte bound thereto are added to the analysis chamber and mixed with the sample. A magnetic pulldown is then performed to separate the magnetic particles with the second analyte bound thereto from the sample. If the reporter is a fluorescence signal reporter, light may then be transmitted through the sample to cause the reporter to fluoresce, and the emitted fluorescence is measured by a suitable detector. In the presence of the analyte of interest, the magnetic particles having the second analyte bound thereto but not being associated with a reporter, are pulled down, resulting in the absence of fluorescence. Depending on the concentration of the analyte of interest in the sample, intensity of the signal generated by the reporter decreases as the analyte concentration increases.

Accordingly, in some embodiments (e.g., in which a second type of the competitive immunoassay method is implemented), the methods described herein may include the steps of: (a) contacting a sample with a reporter conjugate comprising a reporter and a reporter binding moiety configured to bind an analyte of interest the sample; (b) contacting the sample with a magnetic particle-labeled second analyte configured to bind the reporter conjugate in the absence of the analyte of interest in the sample; (c) separating the magnetic particle-labeled analyte from the sample by applying a magnetic field to the sample; and (d) detecting the presence, absence, or level of the analyte by detecting the reporter. The reporter can be detected, e.g., as described in the above embodiments, using a light source and photodetector.

As discussed above, in embodiments of the present disclosure, instead of using a reporter conjugate (i.e. a reporter binding moiety with a reporter bound thereto), a multiplexed detection method can involve use of a reporter binding moiety having a tag bound thereto (instead of a reporter). The reporter binding moiety having a tag bound thereto and a reporter having a corresponding tag binding partner bound thereto can be added to a reaction mixture in two respective separate steps. The use of a reporter binding moiety with a tag bound thereto (and the use of the reporter with a tag binding partner) allows increasing a concentration of a reporter binding moiety, and a concentration of a reporter is substantially lower than the concentration of the reporter binding moiety. The speed of the final complex formation is increased dramatically, such that the entire assay can be performed in less than 20 minutes (e.g., in about 15 minutes), as compared to traditional assay that may take as long as 6 hours.

Accordingly, in some embodiments, a second type of the competitive immunoassay method is a multiplexed immunoassay that involves the use of tags and corresponding tag binding partners for detection of multiple analytes in a sample. The tags and tag binding partners can be selected such that a unique tag-tag binding partner pair is used for detection of a certain analyte of a plurality of analytes. The pair is unique in the context of the detection assay, such that the tag and the tag binding partner, which can bind to one another, do not bind to any other the tag and tag binding partner used in that assay for detection of other analytes of the plurality of analytes.

Accordingly, in some embodiments, the detection method comprises: (a) contacting a sample with a plurality of reporter binding moieties each having a corresponding tag bound thereto, each reporter binding moiety being configured to bind a corresponding analyte of interest of the plurality of analytes; (b) contacting the sample with a plurality of reporters each having a corresponding tag binding partner bound thereto such that the tag binding partner binds a corresponding tag thereby associating a reporter binding moiety bound to the tag with a corresponding reporter, wherein each reporter is configured to generate a corresponding different signal; (c) contacting the sample with a plurality of magnetic particle-labeled second analytes each configured to bind a corresponding reporter binding moiety in the absence of a corresponding analyte of interest of the plurality of analytes; (d) separating the plurality of magnetic particle-labeled analytes from the sample by applying a magnetic field to the sample; and (e) detecting the presence, absence, or level of the analyte based on detection of a signal generated by each of the reporters. The reporter can be detected, e.g., as described in the above embodiments, using a light source and photodetector.

In embodiments, a plurality of analytes of interest can be detected in a biological sample in the multiplexed manner using the competitive immunoassay method. As discussed above, the method may comprise the use of a plurality of reporter binding moieties each having a corresponding tag bound thereto, each reporter binding moiety being configured to bind a corresponding analyte of the plurality of analytes; and of a plurality of reporters each having a corresponding tag binding partner bound thereto such that the tag binding partner binds a corresponding tag, wherein each reporter is configured to generate a corresponding different signal.

In some embodiments, as discussed above, a reporter binding moiety (e.g., a low affinity tag) and a reporter can have respective first and second oligonucleotides bound thereto that can hybridize to one another and thereby facilitate interaction between the reporter binding moiety and reporter. The first and second oligonucleotides can be complementary to one another such that, if there is complementarity, they bind one another and thereby facilitate binding of the tag and the tag binding partner. The tag can have a low affinity to the tag binding partner such that the binding between a first oligonucleotide bound to the tag and a second oligonucleotide bound to the tag binding partner is required for the tag-tag binding partner association and the respective association between a reporter binding moiety and a reporter.

In some embodiments, the tag comprises biotin and the tag binding partner comprises streptavidin, or the tag comprises fluorescein isothiocyanate (FITC) and the tag binding partner comprises anti-FITC antibody, or the tag comprises dinitrophenol (DNP) and the tag binding partner comprises anti-DNP antibody, or the tag comprises digoxigenin (DIG) and the tag binding partner comprises anti-DIG antibody, or the tag comprises Etag and the tag binding partner comprises an anti-Etag antibody (GAPVPYPDPLEPR (SEQ ID NO: 1)), or the tag comprises FLAG and the tag binding partner comprises an anti-FLAG antibody (DYKDDDDK (SEQ ID NO: 2), or the tag comprises Myc and the tag binding partner comprises an anti-Myc antibody (EQKLISEEDL (SEQ ID NO: 3)), or the tag comprises HA and the tag binding partner comprises an anti-HA antibody (YPYDVPDYA (SEQ ID NO: 4), or the tag comprises SNAP and the tag binding partner comprises a benzylguanine derivative, or the tag comprises "CLIP" and the tag binding partner comprises a benzylcytosine derivative.

In some embodiments, the reporter binding moiety has a tag with a short binding half-life (e.g. desthiobiotin) and a first oligonucleotide bound thereto, and the reporter has a tag binding partner comprising avidin (e.g. streptavidin) and a second oligonucleotide bound thereto, wherein the second oligonucleotide is configured to hybridize to the first oligonucleotide when the reporter binding moiety associates with the corresponding reporter via binding between the tag with a short binding half-life bound to the reporter binding moiety and avidin bound to the reporter.

In some embodiments, a method for detecting the presence, absence, or amount of a plurality of analytes in a biological sample may comprise: (a) contacting a sample with a plurality of reporter binding moieties, each reporter binding moiety having a corresponding tag bound thereto and being configured to bind a corresponding analyte of the plurality of analytes; (b) contacting the sample with a plurality of reporters each having a corresponding tag binding partner bound thereto such that the tag binding partner binds a corresponding tag thereby associating a reporter binding moiety bound to the tag with a corresponding reporter, wherein each reporter is configured to generate a corresponding different signal; (c) contacting the sample with a magnetic particle having a plurality of second analytes bound thereto, each being configured to bind a corresponding reporter binding moiety; (d) applying a magnetic field to separate the magnetic particle, optionally having the plurality of second analytes bound thereto; and (e) detecting the presence, absence, or level of the plurality of analytes by detecting the corresponding reporter. The reporter can be detected, e.g., as described in the above embodiments, using a light source and photodetector.

In some embodiments, a tertiary immunoassay method is implemented, which makes use of three binding events to enhance the kinetics of a system used in the present invention. The tertiary binding method can be applied to or can comprise the sandwich method, the separate addition method, and the competitive assay (first and second methods). The tertiary mode may involve the use of a reporter conjugate comprising a reporter having a tag binding partner bound thereto (e.g., fluorescent quantum dot functionalized with streptavidin) and a reporter binding moiety having a tag bound thereto (e.g., an antibody labeled with a biotin), and a magnetic conjugate comprising a magnetic particle and a plurality of capture moieties. The sample can be disposed in an analysis chamber.

The tertiary binding method may comprise adding the magnetic conjugate (comprising a magnetic particle and a plurality of capture moieties) to the analysis chamber and mixing the magnetic conjugate with the sample that may include at least one analyte of interest. A magnetic field may be applied (a "pulldown") to separate the analyte of interest from the sample. Volumes of sample may be removed and analyte concentration steps may be performed one or more times, as described above. The magnetic field may be deactivated and the reporter binding moiety (e.g., an antibody having a tag bound thereto) may be added to the analysis chamber, which may bind to the analyte of interest that is in turn bound to the magnetic conjugate. The reporter (having a tag binding partner bound thereto) may then be added to the analysis chamber, which may then bind to the reporter binding moiety, e.g., via a tag binding partner-tag interaction (e.g., a streptavidin-biotin binding interaction). A magnetic pulldown may then be performed to again separate the analyte of interest from the sample. If the reporter is a fluorescence signal reporter, light may then be transmitted through at least a portion of the analysis chamber to cause the reporter to fluoresce, and the emitted fluorescence is measured by a suitable detector. In the absence of the analyte of interest, no fluorescence occurs.

In some embodiments (e.g., in which a tertiary immunoassay method is implemented), the methods described herein may include steps of: (a) contacting a sample with at least one magnetic conjugate comprising a magnetic particle and a capture moiety configured to bind a corresponding analyte of a plurality of analytes in the sample; (b) applying a magnetic field to separate each of the analytes of the plurality of analytes from the sample; (c) contacting the magnetic conjugate with a plurality of reporter binding moieties each having a corresponding tag bound thereto, each reporter binding moiety being configured to bind a corresponding analyte of the plurality of analytes; (d) contacting the magnetic conjugate with a plurality of reporters each having a corresponding tag binding partner bound that is configured to bind a corresponding tag thereby optionally associating a reporter binding moiety bound to the tag with a corresponding reporter, wherein each reporter is configured to generate a corresponding different signal; (e) applying a magnetic field to separate the magnetic conjugate, optionally having an analyte of the plurality of analytes that has the corresponding reporter binding moiety associated with the corresponding reporter bound thereto; and (f) detecting the presence, absence, or level of each analyte of the plurality of analytes based on detection of a signal generated by each of the reporters.

In the above embodiments, after the step (b) (a pulldown by a magnet to separate the analytes from the sample) is performed, and before the step (c), a magnetic field may be deactivated. Also, in some embodiments, after the step (b) and before the step (c), a volume of a sample may be removed and analyte concentration steps may be performed, as discussed above.

In some embodiments, a multiplexing detection method comprises a whole cell immunoassay in which multiple whole cell analytes of different types (e.g., different bacteria) can be detected simultaneously in the same sample. The whole cell immunoassay targets surface analytes (e.g., biomarkers such as cell surface receptors) present on the cell of interest, thereby detecting the entire cell (e.g., a bacterium). The ability to measure whole cells can provide insights into fitness, immune disorders, cancers, and bacterial infections. In the case of strep throat, e.g. the detection of the bacterium *Streptococcus pyogenes* is highly valuable due to the prevalence of this infection in adults in children. The multiplexed whole cell detection can advantageously allow detecting bacteria in complex samples, which finds use in in clinical, epidemiological, and environmental applications.

In embodiments, the whole cell immunoassay involves the use of, for detection of each analyte, a magnetic conjugate, a plurality of reporter binding moieties, and a plurality of reporters. As in other embodiments described herein, the magnetic conjugate comprises a magnetic particle and a capture moiety coupled to the magnetic particle and configured to bind a corresponding analyte of the plurality of analytes. In some implementations, a magnetic conjugate comprises a magnetic particle that has a plurality of capture moieties coupled thereto, each configured to bind a corresponding analyte of the plurality of analytes. The plurality of reporter binding moieties each have a corresponding tag bound thereto, each reporter binding moiety being configured to bind a corresponding analyte of the plurality of analytes. The one or more capture moieties of the magnetic conjugate and the reporter binding moieties, which can be antibodies specific to surface analytes on the cell of interest, can be configured to bind markers, e.g. cell receptors, on the surface of the cell analyte being detected. The capture moieties and the reporter binding moieties can be configured to bind to the same or different cell surface receptors.

The plurality of reporters each have a corresponding tag binding partner bound thereto such that the tag binding partner can bind a corresponding tag thereby associating a reporter binding moiety bound to the tag with a corresponding reporter. Each reporter is configured to generate a corresponding different signal, e.g., a signal having a different color. The assay can be designed such that, for each type of a cell being detected, multiple magnetic particles and reporters are associated with the cell (via respective capture and reporter binding moieties). For detection of multiple analytes in a multiplexed way, different types of capture and reporter binding moieties, as well as different reporters, are selected for detection of different types of cells, such as, e.g. different bacteria.

In the whole cell multiplexing immunoassay, when the cells of interest are present, the assay components bind the cell receptors on the surface of the cell. The resulting complex can be attracted by a magnet and can provide an optical signal that increases in intensity as the analyte concentration increases. If the cells of interest are absent from the sample, the complex does not form and the reporter system washes away during magnetic pulldown, resulting in a negative signal.

In various embodiments, methods for detecting the presence, absence, or amount of a plurality of analytes in a biological sample can include any of the above-described sandwich method, separate addition method, competitive method (comprising two types), tertiary (three binding event) method, whole cell, or a combination and/or variation of these methods. In some embodiments, one or more of the sandwich, separate addition, competitive, and tertiary methods can be implemented similar to respective assays described in PCT/US2018/015440 (published as WO2018140719), the disclosure of which is incorporated by reference herein in its entirety.

Non-limiting examples of analytes that can be detected by the present methods include one or more of human chorionic gonadotropin (hCG), luteinizing hormone (LH)/Lutropin, prostate specific antigen (PSA), herpes simplex virus (HSV)

antibodies, estrone-3-glucuronide (E3G), bacteria, hemoglobin A1C, C-reactive protein (CRP), an inflammation biomarker, troponin, lyme disease antigen, lyme disease antibodies, an LDL biomarker, an HDL biomarker, a total cholesterol biomarker, thyroid stimulating hormone, a hepatitis C virus biomarker, a rhino virus biomarker, an influenza virus biomarker, a liver function biomarker, estrogen, progesterone, lactic acid, and combinations thereof. In some embodiments, the analyte additionally or alternatively comprises one or more of N-terminal (NT)-pro hormone BNP (NT-proBNP), C-reactive protein (CRP), D-Dimer, Vitamin-D, Vitamin B12, T3, T4, Thyroid-stimulating hormone (TSH), Parathyroid hormone (PTH), Follicle stimulating hormone (FSH), Ferritin, luteinizing hormone (LH), human chorionic gonadotropin (hCG), Progesterone, Estradiol, Testosterone, Prostate-specific antigen (PSA), and Homocysteine, and combinations thereof (e.g. at least 2, or at least 3, or at least 4, or at least 5, or at least 6, or at least 10 of the foregoing).

In some embodiments, the analytes are whole cells, e.g., bacteria, tumor cells, or any other types of cells, e.g. a plurality of whole cells or one type or a variety of types. Embodiments of the present disclosure can also be used to detect viruses or components thereof, e.g. a plurality of viruses or components thereof.

It should be appreciated that embodiments of the present disclosure provide techniques for detection of any suitable analytes.

In embodiments, each analyte of the multiple analytes being detected, if present, becomes associated with a corresponding reporter. Reporters having different properties are used for association with specific analytes. For example, detection of signals of different colors generated by reporters will allow distinguishing between different respective analytes, where a different color corresponds to the respective analyte. The presence, absence, or amount of an analytes can be identified by detecting presence, absence, or different intensity (or other property) of the reporter. In some embodiments, the methods for detecting the presence, absence, or amount of a plurality of analytes of interest in a biological sample can include concentrating the analytes of interest, as described above in connection with a separate addition method. In some embodiments, the methods for detecting the presence, absence, or amount of a plurality of analytes of interest in a biological sample can include some or all steps of one or both of the competitive method, and tertiary (three binding event) method.

The methods in accordance with embodiments of the present disclosure can be implemented in a suitable analysis chamber of an analytic device or system used herein. In some embodiments, the analysis chamber comprises or is a well plate including a suitable number of wells. In embodiments, the multiplexed detecting analysis can be performed in a single well. Thus, each well in a well plate can be used for detection of a plurality of analytes.

The analytic system can include an analysis chamber configured to receive a biological sample therein, a magnet, a light source, and a detector (e.g., a photodetector), among other components. The analytic system can include or can be associated with a magnet, which may be a permanent magnet that may be separated from the analysis chamber in order to apply a magnetic field to the analysis chamber. In some embodiments, the magnet may be an electromagnet that may be controlled to be activated or deactivated in order to apply a magnetic field to the analysis chamber. It should be appreciated that the analytic device or system in accordance with embodiments of the present disclosure can have any suitable configuration and any suitable components configured to detect the presence, absence, or amount of a plurality of analytes in a biological sample.

In some embodiments, the analytic system includes a light source connected to or otherwise associated with the analysis chamber. The light source is configured to transmit light through at least a portion of the analysis chamber.

In some embodiments, the analysis chamber may be one chamber, or two chambers, or three chambers, or four chambers. The analysis chamber may include a plurality of chambers which can be more than four chambers. In some embodiments, the plurality of chambers may be in fluid communication with one another. In some embodiments, one or more of a biological sample, a plurality of reporters, a plurality of reporter binding moieties, a plurality of reporter conjugates (each comprising a reporter and a reporter binding moiety), and a magnetic conjugate (comprising a magnetic particle and one or more capture moieties associated therewith) may be mixed in a first chamber of the plurality of chambers. In some embodiments, the magnetic field may be applied in a second chamber of the plurality of chambers, and a light source coupled to the analysis chamber is configured to transmit light through the second chamber. In some embodiments, the method steps described herein may each be performed in separate chambers of the analysis chamber. In some embodiments, the analysis chamber may be one chamber and all method steps may be performed in the same chamber.

In some embodiments, a photodetector may be connected to or otherwise associated with the analysis chamber (e.g., positioned as facing, in line with, opposite to the light source, or in other ways) and may be configured to detect light transmitted through the analysis chamber by the light source and thereby measure transmittance and/or absorbance of the light. In some embodiments, the photodetector may be positioned relative to the analysis chamber such that the photodetector is orthogonal to the light source (orthogonal illumination), and may be configured to detect fluorescence and/or phosphorescence of a reporter or reporter conjugate in a portion of the analysis chamber. In some embodiments, the photodetector may be positioned relative to the analysis chamber such that the photodetector is opposite to the light source (trans illumination), and may be configured to detect fluorescence and/or phosphorescence of a reporter or reporter conjugate in a portion of the analysis chamber. In some embodiments, the photodetector may be connected to the analysis chamber, in line with the light source (e.g., by way of a dichroic mirror (cis illumination)), and may be configured to detect fluorescence and/or phosphorescence of a reporter or reporter conjugate in a portion of the analysis chamber.

The photodetectors used in embodiments of the present disclosure can have various configurations. In some embodiments, a photodetector may include one or more photomultiplier tube detectors and photodiode detectors. As used herein, the term "photomultiplier" or "photomultiplier tube" refers to optical detection components that convert incident photons into electrons via the photoelectric effect and secondary electron emission. The term photomultiplier tube is meant to include devices that include separate dynodes for current multiplication as well as those devices that include one or more channel electron multipliers. As used herein, the term "optical detector" or "photodetector" refers to a device that generates an output signal when irradiated with optical energy. Thus, in its broadest sense, the term optical detector system is taken to define a device for converting energy from one form to another for the purpose of measurement of a physical quantity or for information transfer. Optical detectors include, but are not limited to, photomultipliers and photodiodes. As used herein, the term "photodiode" refers to a solid-state light detector type including, but not limited to, PN, PIN, APD, CMOS, and CCD. In some embodiments, the photodetector may include one or more of a PN based detector, a PIN based detector, an APD based detector, a CMOS based detector, and a CCD based detector.

In some embodiments, the analysis chamber comprises a photodetector as described herein. In some embodiments, the analysis chamber comprises one or more of a PN based detector, a PIN based detector, an APD based detector, a CMOS based detector, and a CCD based detector.

In various embodiments, an analytic device or system, which can be in the form of a kit, includes a sample collector configured to receive a biological sample obtained from a subject. In various embodiments, the methods in accordance with the present disclosure may involve adding a sample acquired from a subject to the analysis chamber. In some embodiments, adding the sample to the analysis chamber may include delivering the sample to the sample collector. The sample can be blood, plasma or serum, and the sample collector can be or can include a needle prick (e.g. lancet), a syringe, or another form of a sample collector configured to access blood or another bodily fluid. In some implementations, the sample collector can be a retractable element (which can be, e.g., spring-loaded) that can be safely retracted into a sample collection tube or another compartment upon collection of a biological sample (e.g. blood, plasma or serum). In some embodiments, the device for safe sample collection comprises a needle prick (e.g. lancet) or a syringe, wherein the needle prick or the syringe is attached to a cap, the cap is detachably attachable to a sample collection tube. In some embodiments, the needle prick, syringe, or another type of a sample collector is disposed in a removable cover (which can be attached to the device) configured to cover the sample collector when not in use. The removable cover and/or the sample collector can be coupled to a valve or another component configured to be activated to retract the sample collector or otherwise make the sample collector available for sample collection. In some embodiments, the cover can be configured to open automatically, and/or the sample collector can be configured to open automatically.

In some embodiments, the sample collector (e.g., a syringe) is separate from the analytic device or system. The separate sample collector can be part of a kit including the analytic system.

The needle prick, syringe, or another type of a sample collector can be in fluid communication with the interior of the analysis chamber. Thus, the sample collector may provide the sample received therein to the analysis chamber. In some embodiments, the sample collector may include an absorbent and/or wicking material, or another type of a material that facilitates delivery of the collected sample (e.g., blood, plasma or serum) to the analysis chamber.

The analytic device or system can be disposable. In some embodiments, parts of the system (e.g., a sample collector) can be disposable while other parts can be reusable. In some embodiments, some components of the system can be removable and/or disposable.

In some embodiments, one or more of the magnetic conjugate, reporter, reporter binding moiety, and reporter conjugate (comprising a reporter and a reporter binding moiety) may be disposed at the sample collector and the contacting the sample with the magnetic conjugate, reporter, reporter binding moiety, or reporter conjugate may occur at the sample collector. In some embodiments, one or more of the magnetic conjugate, reporter, reporter binding moiety, and reporter conjugate may be imbedded in a portion of the sample collector before a sample is added to the sample collector. In some embodiments, the methods described herein may include contacting the sample in the analysis chamber with a magnetic conjugate, reporter, reporter binding moiety, and/or reporter conjugate.

In some embodiments, the reporter may be a fluorescent reporter, a phosphorescent reporter, or a colorimetric reporter such as a colored particle that may be configured to measure absorbance or scattering of light (or, for example, the presence/absence of a certain color by colorimetric analysis). The reporter can have a tag binding partner such as any of the tag binding partners described hereinabove, or other binding partners, configured to bind to respective tags.

In some embodiments, the methods described herein may further include concentrating analytes of interest in the sample by applying a magnetic field to the analysis chamber after contacting the sample with the magnetic conjugate, and then reducing the volume of the sample in the analysis chamber. In some embodiments, the methods described herein may further include deactivating the magnetic field before contacting the sample with the reporter conjugate.

In some embodiments, reducing the volume of the sample in the analysis chamber may be performed by, for example, syphoning of a fraction of the volume or by removing the entire sample and resuspending the sample in a new, lesser volume.

In embodiments, the methods described herein may further include the steps of concentrating the analytes of interest in the sample by applying a magnetic field to the analysis chamber after contacting the sample with the magnetic conjugate, removing a volume of the sample from the analysis chamber, and adding a volume of buffer and/or an additional volume of the sample to the analysis chamber. In some embodiments, the methods described herein may include the step of deactivating the magnetic field before contacting the sample with the reporter conjugate.

In some embodiments, the methods described herein may include the step of adding a volume of buffer and/or additional volumes of sample to the analysis chamber.

In some embodiments, the methods described herein may include the step of removing volumes of sample from the analysis chamber after a pulldown of the magnetic conjugate (i.e., application of a magnetic field) and before or after contacting the sample with a reporter binding moiety.

In some embodiments, the reporter binding moiety comprises a reporter antibody that is labeled with biotin and the reporter is functionalized with streptavidin. In some embodiments, the reporter binding moiety, such as, e.g., the reporter antibody, is functionalized with streptavidin and the reporter is labeled with biotin.

In any of embodiments in accordance with the present disclosure which can make use of any of the assays described herein (or other suitable assays), tags and tags binding partners (also sometimes referred to as linkers) can be orthogonal such that a tag and a tag binding partner used for detection of a certain analytes of a plurality of analytes are unique (within that assay).

Furthermore, in any of embodiments in accordance with the present disclosure which can make use of any of the assays described herein (or other suitable assays), a reporter binding moiety having a tag associated therewith also has a first oligonucleotide bound thereto, and reporter having a tag binding partner associated therewith also has a second oligonucleotide bound thereto, wherein the second oligonucleotide is configured to hybridize to the first oligonucleotide when the tag interacts with the tag binding partner, thereby associating the reporter binding moiety with the reporter. In such embodiments, the tag is a tag with a short binding half-life (e.g., without limitation, desthiobiotin, its derivate or analogues). The tag binding partner may comprises avidin (e.g. streptavidin), or any other suitable tag binding partner capable of forming an interaction with the tag with a relatively low dissociation constant ($K_d$). For example, the $K_d$ can be at least about 10 times, at least about 50 times, at least about 100 times, or at least about 1000 times, or at least about 10000 times lower than a $K_d$ of biotin/streptavidin association.

In various embodiments, the methods described herein include or make use of various detection techniques, e.g., for detecting a reporter signal. The detection techniques may include use of a microscope, a spectrophotometer, a fluorimeter, a tube luminometer or plate luminometer, x-ray technology, magnetic fields, a scintillator, a fluorescence activated cell sorting (FACS) apparatus, a microfluidics apparatus, a bead-based apparatus, etc.

In some embodiments, a magnetic particle of a magnetic conjugate is a paramagnetic particle. In some embodiments, the paramagnetic particle is a nanoparticle, which can be, e.g., a nanobead. In some embodiments, the paramagnetic particle is a microparticle. In some embodiments, the microparticle is a microbead. The paramagnetic particle is, in various embodiments, a magnetic nano- or microbead, which allows the particle to be held and/or manipulated by magnets. In some embodiments, the paramagnetic particle is a metallic nanoparticles coated with a thin (e.g., about 2 nm in diameter) graphene-like carbon layer. In some embodiments the paramagnetic particle is coated, e.g. streptavidin- or PEG-coated. Examples magnetic particles that can be used are DYNABEADs (THERMOFISHER), MACS beads (MILTENYI BIOTEC), TURBOBEADS (TURBOBEADS), ABSOLUTE MAG STREPTAVIDIN MAGNETIC PARTICLES (CREATIVE DIAGNOSTICS), and GOLD NANOPARTICLES (SIGMAALDRICH).

In some embodiments, the magnetic beads are nanoparticles with a superparamagnetic $Fe_2O_3$ core and a biocompatible outer coating. The surface of the beads can be activated, e.g., with carboxyl groups.

In some embodiments, the reporter particles described herein may include a biocompatible coating that may be activated with amine groups or carboxyl groups to facilitate amid coupling. In some embodiments, the reporter particles described herein may be activated with amine groups or carboxyl groups to facilitate amid coupling.

In some embodiments, the particles described herein may be nanoparticles (e.g. nanobeads), which are smaller than 1 micrometer in diameter (e.g. about 5 to about 500 nanometers, e.g. about 5 nanometers, or about 10 nanometers, or about 50 nanometers, or about 100 nanometers, or about 250 nanometers, or about 500 nanometers). In some embodiments, the nanoparticles (e.g. nanobeads) have a mean particle diameter of 25-500 nm+/−5 nm, 25-500 nm+/−10 nm, 25-500 nm+/−15 nm, 25-500 nm+/−20 nm, 25-500 nm+/−25 nm, 25-500 nm+/−30 nm, 25-500 nm+/−35 nm, 25-500 nm+/−40 nm, 25-500 nm+/−45 nm, or 25-500 nm+/−50 nm. In some embodiments, the nanoparticles (e.g. nanobeads) have a mean particle diameter of about 20 to about 200 nm.

In some embodiments, the nanoparticles (e.g. nanobeads) are smaller than 1 micrometer in diameter (e.g. about 5 to about 500 nanometers, e.g. about 5 nanometers, or about 10 nanometers, or about 50 nanometers, or about 100 nanometers, or about 250 nanometers, or about 500 nanometers). In some embodiments, the nanoparticles (e.g. nanobeads) have a mean particle diameter of 25-500 nm+/−5 nm, 25-500 nm+/−10 nm, 25-500 nm+/−15 nm, 25-500 nm+/−20 nm, 25-500 nm+/−25 nm, 25-500 nm+/−30 nm, 25-500 nm+/−35 nm, 25-500 nm+/−40 nm, 25-500 nm+/−45 nm, or 25-500 nm+/−50 nm. In some embodiments, the nanoparticles (e.g. nanobeads) have a mean particle diameter of about 20 to about 200 nm. In some embodiments, the magnetic particle may be a magnetic nanoparticle (e.g. nanobead) that is composed of oxides, such as ferrites, maghemite, magnetite, or iron oxide, optionally modified by surfactants, silica, silicones or phosphoric acid derivatives. In some embodiments, the nanoparticle (e.g. nanobead) is composed of ferrites with a shell (e.g. a silica shell, optionally modified). In some embodiments, the magnetic nanoparticle is metallic (e.g. iron, cobalt, etc.). In some embodiments, the magnetic nanoparticle is a metallic nanoparticle comprising a shell (e.g. of gentle oxidation, surfactants, polymers and metals (e.g. of gold, graphene, palladium, platinum, etc.).

In some embodiments, a particle described herein may be a nanoparticle that comprises one or more quantum dots. In some embodiments, the nanoparticle comprises a metal core and one or more quantum dots. In some embodiments, the nanoparticle comprises a metal core that may be studded with one or more quantum dots. In some embodiments, the nanoparticle comprises a metal core that may be studded with a plurality of quantum dots. Quantum dots are discrete nanoparticles that have properties similar to bulk semiconductors such that when exposed to electromagnetic energy they in turn emit energy. Quantum dots can be engineered to be sensitive to energy in the infrared region, the visible spectrum, and even ultraviolet range through changes in size and composition. Further, they can be designed to be either photoluminescent or photovoltaic, producing either light or energy, respectively.

In some embodiments, the reporter may be a nanoparticle (e.g. nanobead), which may comprise one or more quantum dots. In some embodiments, the reporter comprises a metal core and one or more quantum dots. In some embodiments, the reporter comprises a metal core that may be studded with one or more quantum dots. In some embodiments, the reporter comprises a metal core that may be studded with a plurality of quantum dots.

In some embodiments, the reporter may comprise one or more quantum dots. In some embodiments, the reporter may comprise one or more quantum dots. In some embodiments, the reporter may comprise a plurality of quantum dots.

Examples of quantum dots, e.g. produced by colloidal methods, include, but are not limited to, cadmium-selenide (CdSe), cadmium-sulfide (CdS), indium-arsenide (InAs), and indium-phosphide (InP) cadmium-tellurium-sulfide (CdTeS). The number of atoms that comprise a quantum dot can range from 100 to 100,000, typically with a diameter ranging from 2 to 20 nm (e.g., 2, 3, 4, 5, 6, 7, 8, 9, 10, 11, 12, 13, 14, 15, 16, 17, 18, 19, 20, 2.5, 3.5, 4.5, 5.5, 6.5, 7.5, 8.5, 9.5, 10.5, 11.5, 12.5, 13.5, 14.5, 15.5, 16.5, 17.5, 18.5, 19.5, 20.5 nm).

In some embodiments, particle materials, including quantum dot materials, include, but are not limited to, carbon, colloidal gold, germanium, indium arsenide, indium antimonide, gallium arsenide, gallium nitride, cadmium/selenium/telluride, lead, lead oxide, lead sulfide, lead selenide, indium gallium phosphide, silicon, colloidal silver, mercury cadmium telluride, iron, iron oxide, cobalt, graphene, lanthanum, cerium, strontium carbonate, manganese, manganese oxide, nickel oxide, platinum, lithium, lithium titanate, tantalum, copper, palladium, molybdenum, boron carbide, silicon carbide, titanium carbide, tungsten oxide, aluminum, niobium, thulium, aluminum nitride, tin, aluminum oxide, tin oxide, antimony, dysprosium, paseodynium, antinmony oxide, erbium, rhenium, barium, ruthenium, beryllium, samarium, bismuth oxide, boron, gadolinium, boron nitride, vanadium oxide, strontium, ytterbium, zirconium, diamond (C), Silicon (Si), germanium (Ge), silicon carbide (SiC), silicon-germanium (SiGe), aluminium antimonide (AlSb), aluminium arsenide (AlAs), aluminium nitride (AlN), aluminium phosphide (AlP), boron nitride (BN), boron phosphide (BP), boron arsenide (BAs), gallium antimonide (GaSb), gallium arsenide (GaAs), gallium nitride (GaN), gallium phosphide (GaP), indium antimonide (InSb), indium arsenide (InAs), indium nitride (InN), indium phosphide (InP), aluminium gallium arsenide (AlGaAs), indium gallium arsenide (InGaAs, InxGai_xAs), indium gallium phosphide (InGaP), aluminum indium arsenide (AlInAs), aluminum indium antimonide (AlInSb), gallium arsenide nitride (GaAsN), gallium arsenide phosphide (GaAsP), aluminum gallium nitride (AlGaN), aluminum gallium phosphide (AlGaP), indium gallium nitride (InGaN), indium arsenide antimonide (InAsSb), indium gallium antimonide (InGaSb), aluminum gallium indium phosphide (AlGaInP, also InAlGaP, InGaAlP, AlInGaP), aluminum gallium arsenide phosphide (AlGaAsP), indium gallium arsenide phosphide (InGaAsP), aluminum indium arsenide phosphide (AlInAsP), aluminum gallium arsenide nitride (AlGaAsN), indium gallium arsenide nitride (InGaAsN), indium aluminium arsenide nitride (InAlAsN), gallium arsenide antimonide nitride (GaAsSbN), gallium indium nitride arsenide antimonide (GaInNAsSb), gallium indium arsenide antimonide phosphide (GaInAsSbP), cadmium selenide (CdSe), cadmium sulfide (CdS), cadmium telluride (CdTe), zinc oxide (ZnO), zinc selenide (ZnSe), zinc sulfide (ZnS), zinc telluride (ZnTe), cadmium zinc telluride (CdZnTe, “CZT”), mercury cadmium telluride (HgCdTe), mercury zinc telluride (HgZnTe), mercury zinc selenide (HgZnSe), cuprous chloride (CuCl), lead selenide (PbSe), lead sulfide (PbS), lead telluride (PbTe), tin sulfide (SnS), tin telluride (SnTe), lead tin telluride (PbSnTe), thallium tin telluride (Ti2SnTe5), thallium germanium telluride (TI2GeTe5), bismuth telluride (Bi2Te3), cadmium phosphide (Cd3P2), cadmium arsenide (Cd3As2), cadmium antimonide (Cd3Sb2), zinc phosphide (Zn3P2), zinc arsenide (Zn3As2), zinc antimonide (Zn3Sb2), lead(II) iodide (Pbl2), molybdenum disulfide (MoS2), gallium selenide (GaSe), tin sulfide (SnS), bismuth sulfide (Bi2S3), copper indium gallium selenide (CIGS), platinum silicide (PtSi), bismuth(III) iodide (Bil3), mercury (II) iodide (Hgl2), thallium(I) bromide (TIBr), titanium dioxide: anatase (TiO2), copper(I) oxide (Cu20), copper(II) oxide (CuO), uranium dioxide (UO2), uranium trioxide (UO3), and the like.

In various embodiments, the magnetic field is applied using an external magnet. In various embodiments, the magnet is a permanent magnet (e.g. neodymium iron boron (NdFeB), samarium cobalt (SmCo), alnico, and ceramic or ferrite magnets). In various embodiments, the magnet is a temporary magnet. In various embodiments, the magnet is an electromagnet.

In various embodiments, the detection of a reporter is undertaken near the magnetic field. In various embodiments, the detection of the reporter is undertaken away from the magnetic field as in, for example, performed in a chamber that is separate from a chamber in which a magnetic pull down step is performed.

In various embodiments, the reporter may be a fluorescent reporter, a phosphorescent reporter, or colorimetric reporter such as a colored particle for measuring absorbance and/or scattering of light (or, for example, the presence absence of a certain color through colorimetric analysis). In some embodiments, any suitable detectable reporter as is known in the art can be used. For example, the detectable reporter can be a radioactive reporter (such as, e.g., 3H, 1251, 35S, 14C, 32P, and 33P), an enzymatic reporter (such as horseradish peroxidase, alkaline phosphatase, glucose 6-phosphate dehydrogenase, and the like), a chemiluminescent reporter (such as e.g., acridinium esters, thioesters, or sulfonamides; luminol, isoluminol, phenanthridinium esters, and the like), a fluorescent reporter (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum or metal containing (Mc) dots (e.g., zinc sulfide-capped cadmium selenide), a thermometric reporter, or an immunopolymerase chain reaction reporter. In various embodiments, the reporter includes without limitation fluorophores, chromophores, radioisotopes, magnetic particles, gold particles, enzyme substrates, and the like. In some embodiments, the reporter is a chemiluminescent or fluorescent protein, such as, for example, green fluorescent protein (GFP), enhanced green fluorescent protein (EGFP), *Renilla Reniformis* green fluorescent protein, GFPmut2, GFPuv4, yellow fluorescent protein (YFP), enhanced yellow fluorescent protein (EYFP), cyan fluorescent protein (CFP), enhanced cyan fluorescent protein (ECFP), enhanced blue fluorescent protein (EBFP), citrine and red fluorescent protein from discosoma (dsRED), luciferase, umbelliferone, rhodamine, fluorescein, dichlorotriazinylamine fluorescein, dansyl chloride, phycoerythrin, and the like. In some embodiments, the reporter is a non-protein organic fluorophore of any of the following families: xanthene derivatives, such as fluorescein, rhodamine, Oregon green, eosin, and Texas red; cyanine derivatives, such as cyanine, indocarbocyanine, oxacarbocyanine, thiacarbocyanine, and merocyanine; squaraine derivatives and ring-substituted squaraines, including Seta, SeTau, and Square dyes; naphthalene derivatives (dansyl and prodan derivatives); coumarin derivatives; oxadiazole derivatives, such as pyridyloxazole, nitrobenzoxadiazole and benzoxadiazole; anthracene derivatives, such as anthraquinones, including DRAQ5, DRAQ7 and CyTRAK Orange; pyrene derivatives, such as cascade blue, etc.; oxazine derivatives, such as Nile red, Nile blue, cresyl violet, oxazine 170, etc.; acridine derivatives, such as proflavin, acridine orange, acridine yellow, etc.; arylmethine derivatives, such as auramine, crystal violet, malachite green; and tetrapyrrole derivatives, such as porphin, phthalocyanine, bilirubin. In various embodiments, the reporter includes without limitation enzymatic reporters, e.g., enzymes such as horseradish peroxidase, alkaline phosphatase, beta-galactosidase, glucose 6-phosphate dehydrogenase, and the like. In some embodiments, the reporter may be a quantum dot as described herein. In some embodiments, the reporter may comprise a quantum dot as described herein. In some embodiments, the reporter may include a metal core (i.e., gold core) with a silica shell, wherein the silica shell is impregnated with a plurality (e.g., 100-600) quantum dots.

In various aspects, the present invention provides a kit suitable for the method of any one of the embodiments disclosed herein. The kit can be for an immunoassay that can simultaneously detect multiple analytes in a sample. The kit may comprise a plurality of magnetic conjugates, a plurality of reporter binding moieties, and a plurality of reporters.

Optionally, the above-described components of the kits of the present technology are packed in suitable containers and labeled for diagnosis of a corresponding disease or condition, or are labeled for corresponding other purpose. The above-mentioned components may be stored in unit or multi-use containers, for example, sealed ampoules, vials, bottles, syringes, and test tubes, as an aqueous, preferably sterile, solution or as a lyophilized, preferably sterile, formulation for reconstitution. For example, the assay reagents of the present technology can be lyophilized to obviate requirement for cold chain shipping and storage. For example, in some embodiments, all reagents except the Magnesium Acetate $Mg(CH_3COO)_2$ are lyophilized in the bottom of the assay tube and the $Mg(CH_3COO)_2$ is lyophilized on the lid: this prevents the 5' to 3' DNA polymerase from occurring until the $Mg(CH_3COO)_2$ is mixed with the other assay reagents.

The kit may further comprise a second container which holds a buffer or other ingredients suitable for diluting the sample towards a higher volume. Furthermore, the kit may comprise instructions for carrying out the assay. The containers may be formed from a variety of materials such as glass or plastic and may have a sterile access. The kit may further comprise more containers comprising an acceptable buffer. The kit may further comprise a device for collecting a biological sample. It may further include other materials desirable from a commercial and user standpoint, including other buffers, diluents, filters, needles, and syringes. The kits may optionally include instructions customarily included in commercial packages of diagnostic products, which include information about, for example, the indications, usage, manufacture, and/or warnings concerning the use of such diagnostic products. The kits may further include a color or fluorescent scale for comparison for diagnosis. The kit components (e.g., reagents) can be packaged in a suitable container. The kit can further comprise instructions for using the kit to detect multiple analytes.

In some embodiments, the kit further comprises a device that collects the biological sample (e.g., blood, serum, plasma, urine, or another type of sample) in a safe manner. In some embodiments (e.g., for analysis of blood content), the device comprises a needle and a safety syringe (e.g. a Luer-type syringe). In some embodiments, the device comprises spring-loaded retractable needle and a syringe. It should be appreciated that the device can be any type of a device for collecting a sample that can be any of whole blood, plasma, serum, bile, saliva, urine, tears, perspiration, cerebrospinal fluid (CSF), semen, mucus, sputum, menstrual blood, menstrual fluid, vaginal mucus, amniotic fluid, synovial fluid, breast milk, ear wax, preejaculate, lochia, Rheum, lymph, and pus. Also, in some embodiments, the kit does not include a sample collection device.

In some embodiments, the kit can also comprise, e.g., a buffering agent, a preservative or a protein-stabilizing agent. The kit can further comprise components necessary for detecting the detectable reporter. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit.

In various aspects, a sample can be obtained from a subject that is a human subject. Additionally, in some embodiments, a subject is a mammal different from a human.

Definitions

The following definitions are used in connection with the invention disclosed herein. Unless defined otherwise, all technical and scientific terms used herein have the same meaning as commonly understood to one of skill in the art to which this invention belongs.

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

As used herein, the term "sample" may refer to a solution, suspension, mixture, or undiluted amount of bodily fluid or another type of fluid that may or may not include an analyte of interest. A sample, as used herein, may include water and/or a buffer.

As used herein, the term "bodily fluid" may refer to any fluid that can be isolated from the body of an individual and includes, but is not limited to whole blood, plasma, serum, bile, saliva, urine, tears, perspiration, cerebrospinal fluid (CSF), semen, swabbed samples (e.g. cheek swabs, throat swabs, etc.), mucus, sputum, menstrual blood, menstrual fluid, vaginal mucus, amniotic fluid, synovial fluid, breast milk, ear wax, preejaculate, lochia, Rheum, lymph, pus, and the like. In some embodiments, bodily fluid may more particularly refer to whole blood, serum, urine, saliva, swabbed samples, mucus, or semen. In certain embodiments, bodily fluid may more particularly refer to whole blood, serum, urine, or saliva. In some embodiments, the bodily fluid may include an analyte of interest (e.g., a biomarker).

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

EXAMPLES

The examples herein are provided to illustrate advantages and benefits of the present technology and to further assist a person of ordinary skill in the art with practicing the method for treating a cancer of the present technology. The examples herein are also presented in order to more fully illustrate the certain aspects of the present technology. The examples should in no way be construed as limiting the scope of the present technology, as defined by the appended claims. The examples can include or incorporate any of the variations, aspects or embodiments of the present technology described above. The variations, aspects or embodiments described above may also further each include or incorporate the variations of any or all other variations, aspects or embodiments of the present technology.

Example 1. Multiplexed Analyte Detection

Figure 4:
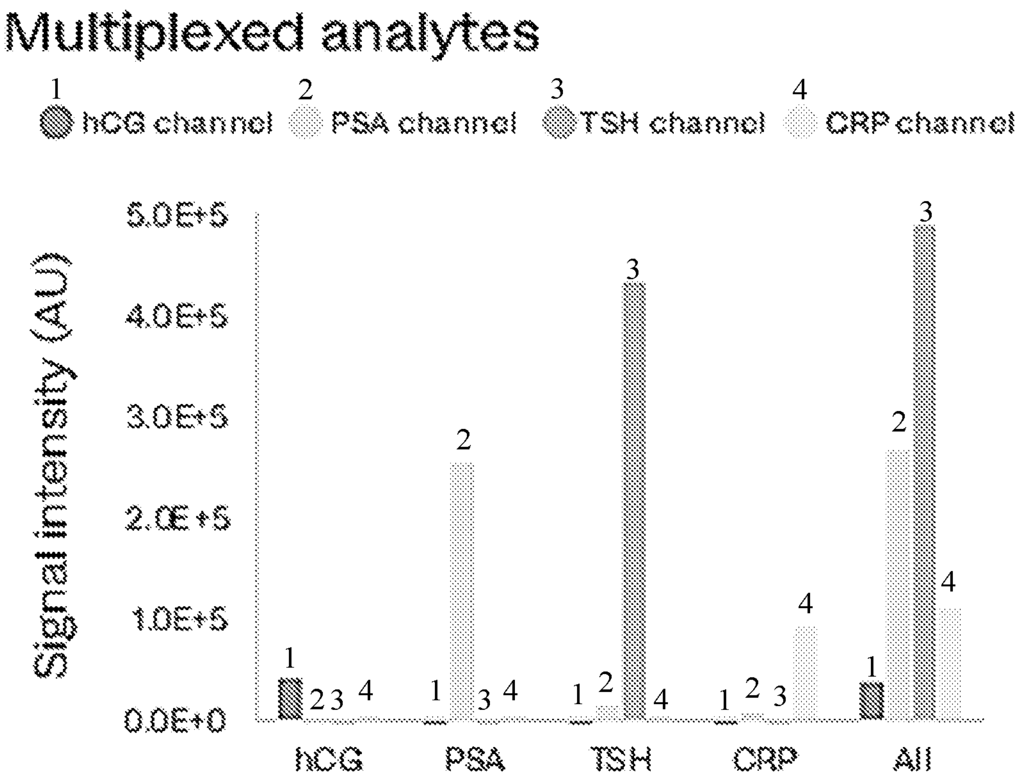
FIG. 4 depicts performance of a multiplexing immunoassay detecting HCG, PSA, TSH, and CRP, in accordance with some embodiments of the present disclosure.

FIG. 4 demonstrates that four analytes can be multiplexed for simultaneous analysis. In this example, hCG, PSA, TSH, and CRP were each spiked into whole blood samples alone, and at the same concentrations simultaneously (All). In FIG. 4 there are four channels (left to right: hCG, PSA, TSH, and CRP). The "All" condition reflects the sample that contains all of hCG, PSA, TSH, and CRP, and the present Example detects all of these analytes in a single experiment. Controls of single analyte conditions are provided to show that, inter alia, the multiplexed detection does not lead a loss of signal.

As shown in FIG. 4, the multiplexing assay in accordance with the present disclosure can simultaneously detect multiple analytes the same biological sample.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

EQUIVALENTS

While the invention has been disclosed in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for detecting the presence, absence, or amount of a plurality of analytes in a biological sample, the method comprising:
   (a) contacting the sample with at least one magnetic conjugate comprising a magnetic particle and a plurality of capture moieties coupled to the magnetic particle and each configured to bind a corresponding analyte of the plurality of analytes;
   (b) contacting the magnetic conjugate with a plurality of reporter binding moieties each having a corresponding tag bound thereto, each reporter binding moiety being configured to bind a corresponding analyte of the plurality of analytes;
   (c) contacting the magnetic conjugate with a plurality of reporters each having a corresponding tag binding partner that is configured to bind a corresponding tag thereby optionally associating a reporter binding moiety with a corresponding reporter, wherein each reporter is configured to generate a corresponding different signal;
   (d) applying a magnetic field to separate the magnetic conjugate, optionally having associated therewith an analyte of the plurality of analytes and the corresponding reporter binding moiety associated with the corresponding reporter bound thereto via a tag-tag binding partner interaction; and
   (e) detecting the presence, absence, or level of each analyte of the plurality of analytes based on detection of the different signals generated corresponding to each of the plurality of reporters, wherein each of the plurality of reporter binding moieties has a first oligonucleotide bound thereto, and each of the plurality of reporters has a second oligonucleotide bound thereto, wherein the second oligonucleotide is configured to hybridize to the first oligonucleotide when the corresponding tag interacts with the corresponding tag binding partner, thereby associating each of the reporter binding moieties with the corresponding reporter.

2. The method of claim 1, wherein the tag comprises biotin and the tag binding partner comprises avidin, or the tag comprises fluorescein isothiocyanate (FITC) and the tag binding partner comprises anti-FITC antibody, or the tag comprises dinitrophenol (DNP) and the tag binding partner comprises anti-DNP antibody, or the tag comprises digoxigenin (DIG) and the tag binding partner comprises anti-DIG antibody, or the tag comprises Etag comprising the sequence SEQ ID NO: 1 and the tag binding partner comprises an anti-Etag antibody, or the tag comprising the sequence SEQ ID NO: 29, and the tag binding partner comprises an antibody that binds SEQ ID NO: 2 antibody, or the tag comprising the sequence SEQ ID NO: 3 and the tag binding partner comprises an antibody that binds SEQ ID NO: 3, or the tag comprises hemagglutinin (HA) comprising the sequence SEQ ID NO: 4, and the tag binding partner comprises an anti-HA antibody, or the tag comprises a mutated eukaryotic DNA methyltransferase and the tag binding partner comprises a benzylguanine derivative or the tag binding partner comprises a benzylcytosine derivative.

3. The method of claim 1, wherein each of the first oligonucleotide and the second oligonucleotide has a length of about 50 nucleotides or less.

4. The method of claim 3, wherein the tag is desthiobiotin and the tag binding partner comprises streptavidin.

5. The method of claim 1, wherein a capture moiety of the plurality of capture moieties of the at least one magnetic conjugate comprises a first antibody configured to bind the corresponding analyte of the plurality of analytes, and wherein a reporter binding moiety comprises a second antibody configured to bind the corresponding analyte.

6. The method of claim 1, wherein the plurality of analytes comprise a plurality of antibodies, and wherein a capture moiety of the at least one magnetic conjugate comprises an antigen configured to bind a corresponding antibody or wherein the plurality of analytes comprise a plurality of protein biomarkers, and wherein a capture moiety of the at least one magnetic conjugate comprises an antibody configured to bind the protein biomarkers.

7. The method of claim 1, wherein a reporter binding moiety of the plurality of reporter binding moieties comprises a secondary antibody configured to bind the antigen.

8. The method of claim 1, wherein the method indicates whether the subject is producing or not producing antibodies directed against an antigen; and/or wherein the method provides an amount of antibodies in the sample.

9. The method of claim 1, wherein the reporter comprises a plurality of quantum dots.

10. The method of claim 1, wherein concentration of the reporter binding moiety is greater than a concentration of the reporter, optionally at least 5 times greater.

11. The method of claim 1, wherein concentration of the reporter binding moiety is greater than concentration of the reporter, optionally at least 10 times greater.

12. The method of claim 1, wherein concentration of the reporter binding moiety is greater than concentration of the reporter, optionally at least 100 times greater.

13. The method of claim 1, wherein concentration of the reporter binding moiety is greater than concentration of the reporter, optionally at least 1000 times greater.

14. The method of claim 1, wherein each reporter of the plurality of reporters is capable of generating a corresponding signal that has at least one property that is different from a property of a signal generated by another reporter of the plurality of reporters.

15. The method of claim 1, wherein the sample is selected from whole blood, plasma, serum, bile, saliva, urine, tears, perspiration, cerebrospinal fluid (CSF), semen, mucus, sputum, menstrual blood, menstrual fluid, vaginal mucus, amniotic fluid, synovial fluid, breast milk, ear wax, preejaculate, lochia, Rheum, lymph, and pus; and/or wherein the sample has a volume of about 1 microliter.

16. The method of claim 1, wherein the plurality of analytes comprise at least four analytes.

17. The method of claim 6, wherein the method further comprises a step of pre-treating the sample with a second magnetic conjugate comprising a magnetic particle and a moiety configured to bind contaminant antibodies and/or non-antibody moieties; and/or wherein the pre-treating reduces or eliminates one or more of:

(a) heterophile antibodies;

(b) antibodies that non-specifically interact with the magnetic particle; and (c) non-antibody moieties that non-specifically interact with the magnetic particle.

18. The method of claim 1, further comprising the step of separating the analyte in the sample from the sample by applying a magnetic field and then reducing the magnetic field before contacting the magnetic conjugate with the plurality of reporter binding moieties.

19. The method of claim 1, wherein the capture moieties and the reporter binding moiety bind different epitopes of the analyte.

20. A multiplexed method for detecting the presence, absence, or amount of a plurality of analytes in a biological sample, the method comprising:

(a) contacting the sample with at least one magnetic conjugate comprising a magnetic particle and a plurality of capture moieties coupled to the magnetic particle and each configured to bind a corresponding analyte of the plurality of analytes;

(b) contacting the magnetic conjugate with a plurality of reporter binding moieties each having a corresponding tag bound thereto, the tag comprising desthiobiotin and each reporter binding moiety being configured to bind a corresponding analyte of the plurality of analytes;

(c) contacting the magnetic conjugate with a plurality of reporters each having a corresponding tag binding partner that is configured to bind a corresponding tag thereby associating a reporter binding moiety with a corresponding reporter, wherein the tag binding partner comprises streptavidin and each reporter is configured to generate a corresponding different signal;

(d) applying a magnetic field to separate the magnetic conjugate, having associated therewith an analyte of the plurality of analytes and the corresponding reporter binding moiety associated with the corresponding reporter bound thereto via a tag-tag binding partner interaction; and (e) detecting the presence, absence, or level of each analyte of the plurality of analytes based on detection of the different signals generated corresponding to each of the plurality of reporters, wherein:

each of the plurality of reporter binding moieties has a first oligonucleotide bound thereto, and each of the plurality of reporters has a second oligonucleotide bound thereto, wherein the second oligonucleotide is configured to hybridize to the first oligonucleotide when the corresponding tag interacts with the corresponding tag binding partner, thereby associating the reporter binding moiety with the reporter; and each of the first oligonucleotide and the second oligonucleotide has a length of about 50 nucleotides or less.

* * * * *

SEQUENCE LISTING

```
<160> NUMBER OF SEQ ID NOS: 26

<210> SEQ ID NO 1
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 1

Gly Ala Pro Val Pro Tyr Pro Asp Pro Leu Glu Pro Arg
1               5                   10


<210> SEQ ID NO 2
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 2

Asp Tyr Lys Asp Asp Asp Asp Lys
1               5
```

<210> SEQ ID NO 3
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 3

Glu Gln Lys Leu Ile Ser Glu Glu Asp Leu
1 5 10

<210> SEQ ID NO 4
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 4

Tyr Pro Tyr Asp Val Pro Asp Tyr Ala
1 5

<210> SEQ ID NO 5
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 5

Ser Arg Leu Glu Glu Glu Leu Arg Arg Arg Leu Thr Glu
1 5 10

<210> SEQ ID NO 6
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 6

Gly Leu Asn Asp Ile Phe Glu Ala Gln Lys Ile Glu Trp His Glu
1 5 10 15

<210> SEQ ID NO 7
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 7

Glu Pro Glu Ala
1

<210> SEQ ID NO 8
<211> LENGTH: 26
<212> TYPE: PRT
<213> ORGANISM: Artificial Sequence
<220> FEATURE:
<223> OTHER INFORMATION: Synthetic Sequence

<400> SEQUENCE: 8

Lys Arg Arg Trp Lys Lys Asn Phe Ile Ala Val Ser Ala Ala Asn Arg
1 5 10 15

```
Phe Lys Lys Ile Ser Ser Ser Gly Ala Leu
            20                  25


<210> SEQ ID NO 9
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 9

Glu Glu Glu Glu Glu Glu
1               5


<210> SEQ ID NO 10
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 10

His His His His His His
1               5


<210> SEQ ID NO 11
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 11

Thr Lys Glu Asn Pro Arg Ser Asn Gln Glu Glu Ser Tyr Asp Asp Asn
1               5                   10                  15

Glu Ser


<210> SEQ ID NO 12
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 12

Thr Glu Thr Ser Gln Val Ala Pro Ala
1               5


<210> SEQ ID NO 13
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 13

Lys Glu Thr Ala Ala Ala Lys Phe Glu Arg Gln His Met Asp Ser
1               5                   10                  15


<210> SEQ ID NO 14
<211> LENGTH: 38
<212> TYPE: PRT
<213> ORGANISM: Artificial Sequence
<220> FEATURE:
<223> OTHER INFORMATION: Synthetic Sequence

<400> SEQUENCE: 14
```

Met Asp Glu Lys Thr Thr Gly Trp Arg Gly Gly His Val Val Glu Gly
1 5 10 15

Leu Ala Gly Glu Leu Glu Gln Leu Arg Ala Arg Leu Glu His His Pro
20 25 30

Gln Gly Gln Arg Glu Pro
35

<210> SEQ ID NO 15
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 15

Pro Asp Arg Val Arg Ala Val Ser His Trp Ser Ser
1 5 10

<210> SEQ ID NO 16
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 16

Trp Ser His Pro Gln Phe Glu Lys
1 5

<210> SEQ ID NO 17
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 17

Met Ala Ser Met Thr Gly Gly Gln Gln Met Gly
1 5 10

<210> SEQ ID NO 18
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 18

Cys Cys Pro Gly Cys Cys
1 5

<210> SEQ ID NO 19
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 19

Glu Val His Thr Asn Gln Asp Pro Leu Asp
1 5 10

<210> SEQ ID NO 20
<211> LENGTH: 14
<212> TYPE: PRT

```
<213> ORGANISM: Artificial Sequence
<220> FEATURE:
<223> OTHER INFORMATION: Synthetic Sequence

<400> SEQUENCE: 20

Gly Lys Pro Ile Pro Asn Pro Leu Leu Gly Leu Asp Ser Thr
1               5                   10


<210> SEQ ID NO 21
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 21

Asp Leu Tyr Asp Asp Asp Asp Lys
1               5


<210> SEQ ID NO 22
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 22

Thr Asp Lys Asp Met Thr Ile Thr Phe Thr Asn Lys Lys Asp Ala Glu
1               5                   10                  15


<210> SEQ ID NO 23
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 23

Ala His Ile Val Met Val Asp Ala Tyr Lys Pro Thr Lys
1               5                   10


<210> SEQ ID NO 24
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 24

Lys Leu Gly Asp Ile Glu Phe Ile Lys Val Asn Lys
1               5                   10


<210> SEQ ID NO 25
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 25

Asp Ile Pro Ala Thr Tyr Glu Phe Thr Asp Gly Lys His Tyr Ile Thr
1               5                   10                  15

Asn Glu Pro Ile Pro Pro Lys
            20


<210> SEQ ID NO 26
```

-continued

```
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 26

Asp Pro Ile Val Met Ile Asp Asn Asp Lys Pro Ile Thr
1               5                   10
```